United States Patent [19]
Joyce et al.

[11] Patent Number: 5,807,718
[45] Date of Patent: Sep. 15, 1998

[54] ENZYMATIC DNA MOLECULES

[75] Inventors: Gerald F. Joyce, Encinitas; Ronald R. Breaker, San Diego, both of Calif.

[73] Assignee: The Scripps Research Institute, La Jolla, Calif.

[21] Appl. No.: 472,194

[22] Filed: Jun. 7, 1995

Related U.S. Application Data

[63] Continuation-in-part of Ser. No. 349,023, Dec. 2, 1994, abandoned.

[51] Int. Cl.$^6$ ............................. C07H 21/04; C12P 19/34
[52] U.S. Cl. ........................................ 435/91.5; 536/24.5
[58] Field of Search ............................... 435/91.1, 91.31, 435/172.3, 320.1, 91.5; 514/44; 536/23.1, 24.5, 23.2

[56] References Cited

FOREIGN PATENT DOCUMENTS

WO 95/11304   4/1995   WIPO .

OTHER PUBLICATIONS

Beaudry and Joyce, *Science*, 257: 635–641 (1992).
Robertson and Joyce, *Nature*, 344: 467 (1990).
Joyce, *Gene*, 82: 83–87 (1989).
Joyce, *Curr. Opin. Struct. Biol.*, 4: 331–336 (1994).
Breaker & Joyce, *Trends Biotech.*, 12: 268–275 (1994).
Breaker, et al., *Biochemistry*, 33: 11980–11986 (1994).
Cadwell and Joyce, *PCR Methods and Applications*, 2: 28–33 (1992).
Cadwell and Joyce, *PCR Methods and Applications*, 3 (Suppl.): s136–s140 (1994).
Joyce and Inoue, *Nucleic Acids Research*, 17: 711–722 (1989).
Lehman and Joyce, *Nature*, 361: 182–185 (1993).
Tsang and Joyce, *Biochemistry* 33: 5966–5973 (1994).
Pan and Uhlenbeck, *Biochemistry*, 31: 3887–3895 (1992).
Pan and Uhlenbeck, *Nature* 358: 560–563 (1992).
Paquette, et al., *Eur. J. Biochem.*, 189: 259–265 (1990).
Perreault, et al., *Nature*, 344: 565–567 (1990).
Williams, et al., *PNAS, USA*, 89: 918–921 (1992).
Yang, et al., *Biochemistry* 31: 5005–5009 (1992).

*Primary Examiner*—George C. Elliott
*Assistant Examiner*—Robert Schwartzman
*Attorney, Agent, or Firm*—Thomas Fitting; Emily Holmes

[57] ABSTRACT

The present invention discloses deoxyribonucleic acid enzymes—catalytic or enzymatic DNA molecules—capable of cleaving nucleic acid sequences or molecules, particularly RNA, in a site-specific manner, as well as compositions including same. Methods of making and using the disclosed enzymes and compositions are also disclosed.

42 Claims, 6 Drawing Sheets

FIG. 3

ENZYMATIC DNA MOLECULES

CROSS-REFERENCE TO RELATED APPLICATION

This is a continuation-in-part of U.S. application Ser. No. 08/349,023, filed Dec. 2, 1994, abandoned the disclosures of which are incorporated by reference herein.

This invention was made with government support under NASA Grant No. NAGW-3118. The government has certain rights in the invention.

TECHNICAL FIELD

The present invention relates to nucleic acid enzymes or catalytic (enzymatic) DNA molecules that are capable of cleaving RNA. The present invention also relates to compositions containing the disclosed enzymatic DNA molecules and to methods of making and using such enzymes and compositions.

BACKGROUND

The need for catalysts that operate outside of their native context or which catalyze reactions that are not represented in nature has resulted in the development of "enzyme engineering" technology. The usual route taken in enzyme engineering has been a "rational design" approach, relying upon the understanding of natural enzymes to aid in the construction of new enzymes. Unfortunately, the state of proficiency in the areas of protein structure and chemistry is insufficient to make the generation of novel biological catalysts routine.

Recently, a different approach for developing novel catalysts has been applied. This method involves the construction of a heterogeneous pool of macromolecules and the application of an in vitro selection procedure to isolate molecules from the pool that catalyze the desired reaction. Selecting catalysts from a pool of macromolecules is not dependent on a comprehensive understanding of their structural and chemical properties. Accordingly, this process has been dubbed "irrational design" (Brenner and Lerner, *PNAS USA* 89: 5381–5383 (1992)).

Most efforts to date involving the rational design of enzymatic RNA molecules or ribozymes have not led to molecules with fundamentally new or improved catalytic function. However, the application of irrational design methods via a process we have described as "directed molecular evolution" or "in vitro evolution", which is patterned after Darwinian evolution of organisms in nature, has the potential to lead to the production of DNA molecules that have desirable functional characteristics.

This technique has been applied with varying degrees of success to RNA molecules in solution (see, e.g., Mills, et al., *PNAS USA* 58: 217 (1967); Green, et al., *Nature* 347: 406 (1990); Chowrira, et al., *Nature* 354: 320 (1991); Joyce, *Gene* 82: 83 (1989); Beaudry and Joyce, *Science* 257: 635–641 (1992); Robertson and Joyce, *Nature* 344: 467 (1990)), as well as to RNAs bound to a ligand that is attached to a solid support (Tuerk, et al., *Science* 249: 505 (1990); Ellington, et al., *Nature* 346: 818 (1990)). It has also been applied to peptides attached directly to a solid support (Lam, et al., *Nature* 354: 82 (1991)); and to peptide epitopes expressed within a viral coat protein (Scott, et al., *Science* 249: 386 (1990); Devlin, et al., *Science* 249: 249 (1990); Cwirla, et al., *PNAS USA* 87: 6378 (1990)).

It has been more than a decade since the discovery of catalytic RNA (Kruger, et al., *Cell* 31: 147–157 (1982); Guerrier-Takada, et al., *Cell* 35: 849–857 (1983)). The list of known naturally-occurring ribozymes continues to grow (see Cech, in *The RNA World*, Gesteland & Atkins (eds.), pp. 239–269, Cold Spring Harbor Laboratory Press, Cold Spring Harbor, N.Y. (1993); Pyle, *Science* 261: 709–714 (1993); Symons, *Curr. Opin. Struct. Biol.* 4: 322–330 (1994)) and, in recent years, has been augmented by synthetic ribozymes obtained through in vitro evolution. (See, e.g., Joyce, *Curr. Opin. Struct. Biol.* 4: 331–336 (1994); Breaker & Joyce, *Trends Biotech.* 12: 268–275 (1994); Chapman & Szostak, *Curr. Onin. Struct. Biol.* 4: 618–622 (1994).)

It seems reasonable to assume that DNA can have catalytic activity as well, considering that it contains most of the same functional groups as RNA. However, with the exception of certain viral genomes and replication intermediates, nearly all of the DNA in biological organisms occurs as a complete duplex, precluding it from adopting a complex secondary and tertiary structure. Thus it is not surprising that DNA enzymes have not been found in nature.

Until the advent of the present invention, the design, synthesis and use of catalytic DNA molecules with nucleotide-cleaving capabilities has not been disclosed or demonstrated. Therefore, the discoveries and inventions disclosed herein are particularly significant, in that they highlight the potential of in vitro evolution as a means of designing increasingly more efficient catalytic molecules, including enzymatic DNA molecules that cleave other nucleic acids, particularly RNA.

BRIEF SUMMARY OF THE INVENTION

The present invention thus contemplates a synthetic (i.e., non-naturally-occurring) catalytic DNA molecule (or enzymatic DNA molecule) capable of cleaving a substrate nucleic acid sequence at a defined cleavage site. The invention also contemplates an enzymatic DNA molecule having an endonuclease activity.

In one preferred variation, the endonuclease activity is specific for a nucleotide sequence defining a cleavage site comprising single-stranded nucleic acid in the substrate nucleic acid sequence. In another preferred variation, the cleavage site is a double-stranded nucleic acid.

In another contemplated embodiment, the substrate nucleic acid sequence includes one or more nucleotide analogues. In one variation, the substrate nucleic acid sequence is a portion of a larger molecule.

In various embodiments, the larger molecule is selected from the group consisting of RNA, modified RNA, DNA, modified DNA, nucleotide analogs, or composites thereof. In another example, the larger molecule comprises a composite of a nucleic acid sequence and a non-nucleic acid sequence.

In another embodiment, the invention contemplates that a substrate nucleic acid sequence includes one or more nucleotide analogs. A further variation contemplates that the single stranded nucleic acid comprises RNA, DNA, modified RNA, modified DNA, one or more nucleotide analogs, or any composite thereof. In one embodiment of the disclosed invention, the endonuclease activity comprises hydrolytic cleavage of a phosphoester bond at the cleavage site.

In various preferred embodiments, the catalytic DNA molecules of the present invention are single-stranded. These catalytic DNA molecules may preferably assume a variety of shapes consistent with their catalytic activity. Thus, in one variation, a catalytic DNA molecule of the present invention includes one or more hairpin loop structures. In yet another variation, a catalytic DNA molecule may assume a shape similar to that of "hammerhead" ribozymes.

Similarly, preferred catalytic DNA molecules of the present invention are able to demonstrate site-specific endonuclease activity irrespective of the original orientation of the substrate molecule. That is, in one preferred embodiment, an enzymatic DNA molecule of the present invention is able to cleave a substrate nucleic acid sequence that is separate from the enzymatic DNA molecule—i.e., it is not linked to the DNAzyme. In another preferred embodiment, an enzymatic DNA molecule is able to cleave an attached substrate nucleic acid sequence—i.e., it is able to perform a type of self-cleavage.

The invention also contemplates enzymatic DNA molecules (catalytic DNA molecules or DNAzymes) having endonuclease activity, whereby the endonuclease activity requires the presence of a divalent cation. In various preferred, alternative embodiments, the divalent cation is selected from the group consisting of $Pb^{2+}$, $Mg^{2+}$, $Mn^{2+}$, $Zn^{2+}$, and $Ca^{2+}$. Another variation contemplates that the endonuclease activity requires the presence of a monovalent cation. In such alternative embodiments, the monovalent cation is preferably selected from the group consisting of $Na^+$ and $K^+$.

In various preferred embodiments of the invention, an enzymatic DNA molecule comprises a nucleotide sequence selected from the group consisting of SEQ ID NO 3, SEQ ID NO 14; SEQ ID NO 15; SEQ ID NO 16; SEQ ID NO 17; SEQ ID NO 18; SEQ ID NO 19; SEQ ID NO 20; SEQ ID NO 21; and SEQ ID NO 22. In other preferred embodiments, a catalytic DNA molecule of the present invention comprises a nucleotide sequence selected from the group consisting of SEQ ID NO 23; SEQ ID NO 24; SEQ ID NO 25; SEQ ID NO 26; SEQ ID NO 27; SEQ ID NO 28; SEQ ID NO 29; SEQ ID NO 30; SEQ ID NO 31; SEQ ID NO 32; SEQ ID NO 33; SEQ ID NO 34; SEQ ID NO 35; SEQ ID NO 36; SEQ ID NO 37; SEQ ID NO 38; and SEQ ID NO 39.

In a further variation of the present invention, an enzymatic DNA molecule of the present invention preferably has a substrate binding affinity of about 1 µM or less. In another embodiment, an enzymatic DNA molecule of the present invention binds substrate with a $K_D$ of less than about 0.1 µM.

The present invention also contemplates an embodiment whereby the nucleotide sequence defining the cleavage site comprises at least one nucleotide. In various other preferred embodiments, a catalytic DNA molecule of the present invention is able to recognize and cleave a nucleotide sequence defining a cleavage site of two or more nucleotides.

In various preferred embodiments, an enzymatic DNA molecule of the present invention comprises a conserved core flanked by one or more substrate binding regions. In one embodiment, an enzymatic DNA molecule includes first and second substrate binding regions. In another embodiment, an enzymatic DNA molecule includes two or more substrate binding regions.

As noted previously, preferred catalytic DNA molecules of the present invention also include a conserved core. In one preferred embodiment, the conserved core comprises one or more conserved regions. In other preferred variations, the one or more conserved regions include a nucleotide sequence selected from the group consisting of CG; CGA; AGCG; AGCCG; CAGCGAT; CTTGTTT; and CTTATTT.

In one embodiment of the invention, an enzymatic DNA molecule of the present invention further comprises one or more variable or spacer nucleotides between the conserved regions in the conserved core. In another embodiment, an enzymatic DNA molecule of the present invention further comprises one or more variable or spacer nucleotides between the conserved core and the substrate binding region.

In one variation, the first substrate binding region preferably includes a nucleotide sequence selected from the group consisting of CATCTCT; GCTCT; TTGCTTTTT; TGTCTTCTC; TTGCTGCT; GCCATGCTTT (SEQ ID NO 19, residues 5–14); CTCTATTTCT (SEQ ID NO 20, residues 10–19); GTCGGCA; CATCTCTTC; and ACTTCT. In another preferred variation, the second substrate binding region includes a nucleotide sequence selected from the group consisting of TATGTGACGCTA (SEQ ID NO 14, residues 28–39); TATAGTCGTA (SEQ ID NO 15, residues 41–50); ATAGCGTATTA (SEQ ID NO 16, residues 40–50); ATAGTTACGTCAT (SEQ ID NO 17, residues 27–39); AATAGTGAAGTGTT (SEQ ID NO 18, residues 28–41); TATAGTGTA; ATAGTCGGT; ATAGGCCCGGT (SEQ ID NO 21, residues 40–50); AATAGTGAGGCTTG (SEQ ID NO 22, residues 36–49); and ATGNTG.

In another preferred embodiment, a catalytic DNA molecule of the present invention may further comprise a third substrate binding region. In some preferred embodiments, the third region includes a nucleotide sequence selected from the group consisting of TGTT; TGTTA; and TGTTAG. Another preferred embodiment of the present invention discloses an enzymatic DNA molecule further comprising one or more variable or "spacer" regions between the substrate binding regions.

In another disclosed embodiment, the present invention contemplates a purified, synthetic enzymatic DNA molecule separated from other DNA molecules and oligonucleotides, the enzymatic DNA molecule having an endonuclease activity, wherein the endonuclease activity is specific for a nucleotide sequence defining a cleavage site comprising single-stranded nucleic acid in a substrate nucleic acid sequence. In one variation, a synthetic enzymatic DNA molecule having an endonuclease activity is disclosed, wherein the endonuclease activity is specific for a nucleotide sequence defining a cleavage site consisting essentially of a single-stranded region of a substrate nucleic acid sequence.

In yet another embodiment, the invention contemplates an enzymatic DNA molecule comprising a deoxyribonucleotide polymer having a catalytic activity for hydrolyzing a nucleic acid-containing substrate to produce substrate cleavage products. In one variation, the hydrolysis takes place in a site-specific manner. In another variation, the polymer is single-stranded; another embodiment contemplates that the substrate includes a single-stranded segment.

The invention further contemplates that the substrate comprises a nucleic acid sequence. In various embodiments, the nucleic acid sequence substrate comprises RNA, modified RNA, DNA, modified DNA, one or more nucleotide analogs, or composites of any of the foregoing.

The present invention further contemplates an enzymatic DNA molecule comprising a deoxyribonucleotide polymer having a catalytic activity for hydrolyzing a nucleic acid-containing substrate to produce a cleavage product. In one variation, the enzymatic DNA molecule has an effective binding affinity for the substrate and lacks an effective binding affinity for the cleavage product.

In one preferred embodiment, the invention discloses a non-naturally-occurring enzymatic DNA molecule comprising a nucleotide sequence defining a conserved core flanked by recognition domains, variable regions, and spacer regions. Thus, in one preferred embodiment, the nucleotide sequence defines a first variable region contiguous or adjacent to the 5'-terminus of the molecule, a first recognition domain located 3'-terminal to the first variable region, a first spacer region located 3'-terminal to the first recognition domain, a first conserved region located 3'-terminal to the first spacer region, a second spacer region located 3'-terminal to the first conserved region, a second conserved region located 3'-terminal to the second spacer region, a second recognition domain located 3'-terminal to the second conserved region, and a second variable region located 3'-terminal to the second recognition domain.

In another embodiment, the nucleotide sequence preferably defines a first variable region contiguous or adjacent to the 5'-terminus of the molecule, a first recognition domain located 3'-terminal to the first variable region, a first spacer region located 3'-terminal to the first recognition domain, a first conserved region located 3'-terminal to the first spacer region, a second spacer region located 3'-terminal to the first conserved region, a second conserved region located 3'-terminal to the second spacer region, a second recognition domain located 3'-terminal to the second conserved region, a second variable region located 3'-terminal to the second recognition domain, and a third recognition domain located 3'-terminal to the second variable region.

In one variation of the foregoing, the molecule includes a conserved core region flanked by two substrate binding domains; in another, the conserved core region comprises one or more conserved domains. In other preferred embodiments, the conserved core region further comprises one or more variable or spacer nucleotides. In yet another embodiment, an enzymatic DNA molecule of the present invention further comprises one or more spacer regions.

The present invention further contemplates a wide variety of compositions. For example, compositions including an enzymatic DNA molecule as described hereinabove are disclosed and contemplated herein. In an alternative embodiment, a composition according to the present invention comprises two or more populations of enzymatic DNA molecules as described above, wherein each population of enzymatic DNA molecules is capable of cleaving a different sequence in a substrate. In another variation, a composition comprises two or more populations of enzymatic DNA molecules as described hereinabove, wherein each population of enzymatic DNA molecules is capable of recognizing a different substrate. In various embodiments, it is also preferred that compositions include a monovalent or divalent cation.

The present invention further contemplates methods of generating, selecting, and isolating enzymatic DNA molecules of the present invention. In one variation, a method of selecting enzymatic DNA molecules that cleave a nucleic acid sequence (e.g., RNA) at a specific site, comprises the following steps: (a) obtaining a population of synthetic, single-stranded DNA molecules; (b) admixing nucleotide-containing substrate sequences with the population of single-stranded DNA molecules to form an admixture; (c) maintaining the admixture for a sufficient period of time and under predetermined reaction conditions to allow single-stranded DNA molecules in the population to cause cleavage of the substrate sequences, thereby producing substrate cleavage products; (d) separating the population of single-stranded DNA molecules from the substrate sequences and substrate cleavage products; and (e) isolating single-stranded DNA molecules that cleave substrate nucleic acid sequences (e.g., RNA) at a specific site from the population.

In a further variation of the foregoing method, the DNA molecules that cleave substrate nucleic acid sequences at a specific site are tagged with an immobilizing agent. In one example, the agent comprises biotin.

The invention also contemplates methods as described above, wherein the isolating step further comprises exposing the tagged DNA molecules to a solid surface having avidin linked thereto, whereby the tagged DNA molecules become attached to the solid surface. As before, the substrate may be RNA, DNA, a composite of both, or a molecule including nucleotide sequences.

The present invention also contemplates a method for specifically cleaving a substrate nucleic acid sequence at a particular cleavage site, comprising the steps of (a) providing an enzymatic DNA molecule capable of cleaving a substrate nucleic acid sequence at a specific cleavage site; and (b) contacting the enzymatic DNA molecule with the substrate nucleic acid sequence to cause specific cleavage of the nucleic acid sequence at the cleavage site. In one variation, the enzymatic DNA molecule is a non-naturally-occurring (or synthetic) DNA molecule. In another variation, the enzymatic DNA molecule is single-stranded.

In still another variation, of the foregoing method, the substrate comprises a nucleic acid. In various embodiments, the substrate nucleic acid comprises RNA, modified RNA, DNA, modified DNA, one or more nucleotide analogs, or composites of any of the foregoing. In yet another embodiment, the specific cleavage is caused by the endonuclease activity of the enzymatic DNA molecule.

The present invention also contemplates a method of cleaving a phosphoester bond, comprising (a) admixing an catalytic DNA molecule capable of cleaving a substrate nucleic acid sequence at a defined cleavage site with a phosphoester bond-containing substrate, to form a reaction admixture; and (b) maintaining the admixture under predetermined reaction conditions to allow the enzymatic DNA molecule to cleave the phosphoester bond, thereby producing a population of substrate products. In one embodiment, the enzymatic DNA molecule is able to cleave the phosphoester bond in a site-specific manner. In another embodiment, the method further comprises the steps of (c) separating the products from the catalytic DNA molecule; and (d) adding additional substrate to the enzymatic DNA molecule to form a new reaction admixture.

The present invention also contemplates methods of engineering enzymatic DNA molecules that cleave phosphoester bonds. One exemplary method comprises the following steps: (a) obtaining a population of single-stranded DNA molecules; (b) introducing genetic variation into the population to produce a variant population; (c) selecting individuals from the variant population that meet predetermined selection criteria; (d) separating the selected individuals from the remainder of the variant population; and (e) amplifying the selected individuals.

BRIEF DESCRIPTION OF THE DRAWINGS

FIG. 3 illustrates the sequence alignment of individual variants isolated from the population after five rounds of selection. The fixed substrate domain is shown at the top, with the target riboadenylate identified via an inverted triangle. Substrate nucleotides that are commonly involved in presumed base-pairing interactions are indicated by vertical bars. Sequences corresponding to the 50 initially-randomized nucleotides are aligned antiparallel to the substrate domain. All of the variants are 3'-terminated by the fixed sequence 5'-CGGTAAGCTTGGCAC-3'(not shown; SEQ ID NO 1). Nucleotides within the initially-randomized region that are presumed to form base pairs with the substrate domain are indicated on the right and left sides of the Figure; the putative base-pair-forming regions of the enzymatic DNA molecules are individually boxed in each sequence shown. Conserved regions are illustrated via the two large, centrally-located boxes.

FIG. 4A is a diagrammatic representation of the complex formed between the 19mer substrate (3'-TCACTATrAGGAAGAGATGG-5', SEQ ID NO 2) and 38mer DNA enzyme (5'-ACACATCTCTGAAGTAGCGCCGCCGTATAGTGACG CTA-3', SEQ ID NO 3). The substrate contains a single adenosine ribonucleotide ("rA", adjacent to the arrow), flanked by deoxyribonucleotides. The synthetic DNA enzyme is a 38-nucleotide portion of the most frequently occurring variant shown in FIG. 3. Highly-conserved nucleotides located within the putative catalytic domain are "boxed". As illustrated, one conserved sequence is "AGCG", while another is "CG" (reading in the 5'→3' direction).

FIG. 4B shows an Eadie-Hofstee plot used to determine $K_m$ (negative slope) and $V_{max}$ (y-intercept) for DNA-catalyzed cleavage of [5'-$^{32}$P]-labeled substrate under conditions identical to those employed during in vitro selection. Initial rates of cleavage were determined for reactions involving 5 nM DNA enzyme and either 0.125, 0.5, 1, 2, or 4 µM substrate.

As noted, there are three lanes within each of the aforementioned four groups. In each group of three lanes, the first lane shows the lack of activity of the selected population in the absence of the metal cation, the second lane shows the observed activity in the presence of the metal cation, and the third lane shows the lack of activity of the starting pool (G0).

Figure 6A:
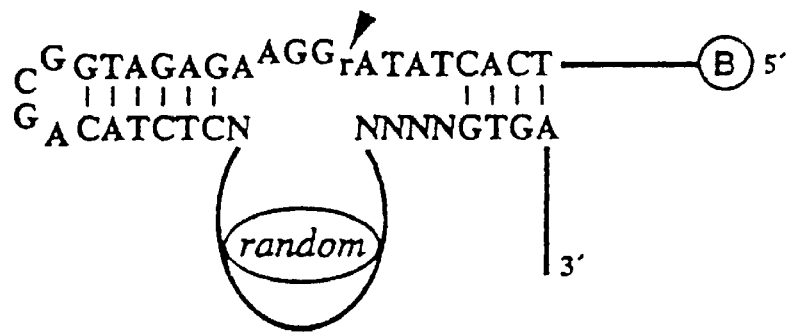
Figure 6B:
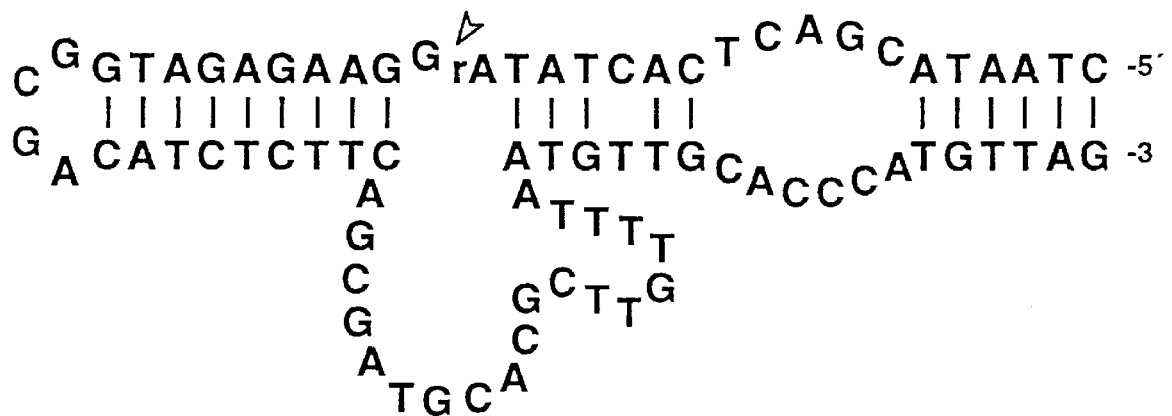

FIGS. 6A and 6B provide two-dimensional illustrations of a "progenitor" catalytic DNA molecule and one of several catalytic DNA molecules obtained via the selective amplification methods disclosed herein, respectively. FIG. 6A illustrates an exemplary molecule from the starting pool, showing the overall configuration of the molecules represented by SEQ ID NO 23. As illustrated, various complementary nucleotides flank the random ($N_{40}$) region. FIG. 6B is a diagrammatic representation of one of the $Mg^{2+}$-dependent catalytic DNA molecules (or "DNAzymes") generated via the within-described procedures (SEQ ID NO 40). The location of the ribonucleotide in the substrate nucleic acid is indicated via the arrow in both FIGS. 6A and 6B.

DETAILED DESCRIPTION

A. Definitions

As used herein, the term "deoxyribozyme" is used to describe a DNA-containing nucleic acid that is capable of functioning as an enzyme. In the present disclosure, the term "deoxyribozyme" includes endoribonucleases and endodeoxyribonucleases, although deoxyribozymes with endoribonuclease activity are particularly preferred. Other terms used interchangeably with deoxyribozyme herein are "enzymatic DNA molecule" or "catalytic DNA molecule", which should be understood to include enzymatically active portions thereof, whether they are produced synthetically or derived from organisms or other sources.

The term "enzymatic DNA molecules" also includes DNA molecules that have complementarity in a substrate-binding region to a specified oligonucleotide target or substrate; it also has an enzymatic activity which is active to specifically cleave the oligonucleotide substrate. Stated in another fashion, the enzymatic DNA molecule is capable of cleaving the oligonucleotide substrate intermolecularly. This complementarity functions to allow sufficient hybridization of the enzymatic DNA molecule to the substrate oligonucleotide to allow the intermolecular cleavage of the substrate to occur. While one-hundred percent (100%) complementarity is preferred, complementarity in the range of 75–100% is also useful and contemplated by the present invention.

Enzymatic DNA molecules of the present invention may alternatively be described as having nuclease or ribonuclease activity. These terms may be used interchangeably herein.

The term "enzymatic nucleic acid" as used herein encompasses enzymatic RNA or DNA molecules, enzymatic RNA-DNA polymers, and enzymatically active portions or derivatives thereof, although enzymatic DNA molecules are a particularly preferred class of enzymatically active molecules according to the present invention.

The term "endodeoxyribonuclease", as used herein, is an enzyme capable of cleaving a substrate comprised predominantly of DNA. The term "endoribonuclease", as used herein, is an enzyme capable of cleaving a substrate comprised predominantly of RNA.

As used herein, the term "base pair"(bp) is generally used to describe a partnership of adenine (A) with thymine (T) or uracil (U), or of cytosine (C) with guanine (G), although it should be appreciated that less-common analogs of the bases A, T, C, and G may occasionally participate in base pairings.

Nucleotides that normally pair up when DNA or RNA adopts a double stranded configuration may also be referred to herein as "complementary bases".

"Complementary nucleotide sequence" generally refers to a sequence of nucleotides in a single-stranded molecule of DNA or RNA that is sufficiently complementary to that on another single oligonucleotide strand to specifically hybridize to it with consequent hydrogen bonding.

"Nucleotide" generally refers to a monomeric unit of DNA or RNA consisting of a sugar moiety (pentose), a phosphate group, and a nitrogenous heterocyclic base. The base is linked to the sugar moiety via the glycosidic carbon (1'carbon of the pentose) and that combination of base and sugar is a "nucleoside". When the nucleoside contains a phosphate group bonded to the 3' or 5' position of the pentose, it is referred to as a nucleotide. A sequence of operatively linked nucleotides is typically referred to herein as a "base sequence" or "nucleotide sequence", and their grammatical equivalents, and is represented herein by a formula whose left to right orientation is in the conventional direction of 5'-terminus to 3'-terminus, unless otherwise specified.

"Nucleotide analog" generally refers to a purine or pyrimidine nucleotide that differs structurally from A, T, G, C, or U, but is sufficiently similar to substitute for the normal nucleotide in a nucleic acid molecule. As used herein, the term "nucleotide analog" encompasses altered bases, different sugars, or a combination of the two. A listing of exemplary analogs wherein the base has been altered is provided in section C hereinbelow.

"Oligonucleotide or polynucleotide" generally refers to a polymer of single- or double-stranded nucleotides. As used herein, "oligonucleotide" and its grammatical equivalents will include the full range of nucleic acids. An oligonucleotide will typically refer to a nucleic acid molecule comprised of a linear strand of ribonucleotides. The exact size will depend on many factors, which in turn depends on the ultimate conditions of use, as is well known in the art.

As used herein, the term "physiologic conditions" is meant to suggest reaction conditions emulating those found in mammalian organisms, particularly humans. While variables such as temperature, availability of cations, and pH ranges may vary as described in greater detail below, "physiologic conditions" generally comprise a temperature of about 35°–40° C., with 37° C. being particularly preferred, as well as a pH of about 7.0–8.0, with 7.5 being particularly preferred, and further comprise the availability of cations, preferably divalent and/or monovalent cations, with a concentration of about 2–15 mM $Mg^{2+}$ and 0–1.0M Na+ being particularly preferred. "Physiologic conditions", as used herein, may optionally include the presence of free nucleoside cofactor. As noted previously, preferred conditions are described in greater detail below.

B. Enzymatic DNA Molecules

In various embodiments, an enzymatic DNA molecule of the present invention may combine one or more modifications or mutations including additions, deletions, and substitutions. In alternative embodiments, such mutations or modifications may be generated using methods which produce random or specific mutations or modifications. These mutations may, for example, change the length of, or alter the nucleotide sequence of, a loop, a spacer region or the recognition sequence (or domain). One or more mutations within one catalytically active enzymatic DNA molecule may be combined with the mutation(s) within a second catalytically active enzymatic DNA molecule to produce a new enzymatic DNA molecule containing the mutations of both molecules.

In other preferred embodiments, an enzymatic DNA molecule of the present invention may have random mutations introduced into it using a variety of methods well known to those skilled in the art. For example, the method described by Cadwell and Joyce (*PCR Methods and Applications* 2: 28–33 (1992)) is particularly preferred for use as disclosed herein, with some modifications, as described in the Examples that follow. (Also see Cadwell and Joyce, *PCR Methods and Applications* 3 (Suppl.): S136–S140 (1994).) According to this modified PCR method, random point mutations may be introduced into cloned genes.

The method has been used, for example, to mutagenize the gene encoding the ribozyme with a mutation rate of 0.66%±0.13% (95% confidence interval) per position, as determined by sequence analysis, with no strong preferences observed with respect to the type of base substitution. This allows the introduction of random mutations at any position in the molecule.

Another method useful in introducing defined or random mutations is disclosed in Joyce and Inoue, *Nucleic Acids Research* 17: 711–722 (1989). This latter method involves excision of a template (coding) strand of a double-stranded DNA, reconstruction of the template strand with inclusion of mutagenic oligonucleotides, and subsequent transcription of the partially-mismatched template. This allows the introduction of defined or random mutations at any position in the molecule by including polynucleotides containing known or random nucleotide sequences at selected positions.

Enzymatic DNA molecules of the present invention may be of varying lengths and folding patterns, as appropriate, depending on the type and function of the molecule. For example, enzymatic DNA molecules may be about 15 to about 400 or more nucleotides in length, although a length not exceeding about 250 nucleotides is preferred, to avoid limiting the therapeutic usefulness of molecules by making them too large or unwieldy. In various preferred embodiments, an enzymatic DNA molecule of the present invention is at least about 20 nucleotides in length, and is preferably not more than about 100 nucleotides in length.

In various therapeutic applications, enzymatic DNA molecules of the present invention comprise the enzymatically active portions of deoxyribozymes. In various embodiments, enzymatic DNA molecules of the present invention preferably comprise not more than about 200 nucleotides. In other embodiments, a deoxyribozyme of the present invention comprises not more than about 100 nucleotides, more preferably, not more than about 50 nucleotides in length.

In other applications, enzymatic DNA molecules may assume configurations similar to those of "hammerhead" ribozymes. Such enzymatic DNA molecules are preferably no more than about 100 nucleotides in length, with a length of about 20–50 nucleotides being particularly preferred.

In general, if one intends to synthesize molecules for use as disclosed herein, the larger the enzymatic nucleic acid molecule is, the more difficult it is to synthesize. Those of skill in the art will certainly appreciate these design constraints.

It is also to be understood that an enzymatic DNA molecule of the present invention may comprise enzymatically active portions of a deoxyribozyme or may comprise a deoxyribozyme with one or more mutations, e.g., with one or more base-pair-forming sequences or spacers absent or modified, as long as such deletions, additions or modifications do not adversely impact the molecule's ability to perform as an enzyme.

The recognition domain of an enzymatic DNA molecule of the present invention typically comprises two nucleotide sequences flanking a catalytic domain, and typically contains a sequence of at least about 3 to about 30 bases, preferably about 6 to about 15 bases, which are capable of hybridizing to a complementary sequence of bases within the substrate nucleic acid giving the enzymatic DNA molecule its high sequence specificity. Modification or mutation of the recognition site via well-known methods allows one to alter the sequence specificity of an enzymatic nucleic acid molecule. (See, e.g, Joyce et al., *Nucleic Acids Research*, 17:711–712 (1989).)

Enzymatic nucleic acid molecules of the present invention include those with altered recognition sites or domains. In various embodiments, these altered recognition domains confer unique sequence specificities on the enzymatic nucleic acid molecule including such recognition domains. The exact bases present in the recognition domain determine the base sequence at which cleavage will take place. Cleavage of the substrate nucleic acid occurs within the recognition domain. This cleavage leaves a 2', 3', or 2', 3'-cyclic phosphate group on the substrate cleavage sequence and a 5' hydroxyl on the nucleotide that was originally immediately 3' of the substrate cleavage sequence in the original substrate. Cleavage can be redirected to a site of choice by changing the bases present in the recognition sequence (internal guide sequence). See Murphy et al., *Proc. Natl. Acad. Sci. USA* 86: 9218–9222 (1989).

Moreover, it may be useful to add a polyamine to facilitate recognition and binding between the enzymatic DNA molecule and its substrate. Examples of useful polyamines include spermidine, putrescine or spermine. A spermidine concentration of about 1 mM may be effective in particular embodiments, while concentrations ranging from about 0.1 mM to about 10 mM may also be useful.

In various alternative embodiments, an enzymatic DNA molecule of the present invention has an enhanced or optimized ability to cleave nucleic acid substrates, preferably RNA substrates. As those of skill in the art will appreciate, the rate of an enzyme-catalyzed reaction varies depending upon the substrate and enzyme concentrations and, in general, levels off at high substrate or enzyme concentrations. Taking such effects into account, the kinetics of an enzyme-catalyzed reaction may be described in the following terms, which define the reaction.

The enhanced or optimized ability of an enzymatic DNA molecule of the present invention to cleave an RNA substrate may be determined in a cleavage reaction with varying amounts of labeled RNA substrate in the presence of enzymatic DNA molecule. The ability to cleave the substrate is generally defined by the catalytic rate ($k_{cat}$) divided by the Michaelis constant ($K_M$). The symbol $k_{cat}$ represents the maximal velocity of an enzyme reaction when the substrate approaches a saturation value. $K_M$ represents the substrate concentration at which the reaction rate is one-half maximal.

For example, values for $K_M$ and $k_{cat}$ may be determined in this invention by experiments in which the substrate concentration [S] is in excess over enzymatic DNA molecule concentration [E]. Initial rates of reaction ($v_0$) over a range of substrate concentrations are estimated from the initial linear phase, generally the first 5% or less of the reaction. Data points are fit by a least squares method to a theoretical line given by the equation: $v = -K_M(v_0/[S]) + V_{max}$. Thus, $k_{cat}$ and $K_M$ are determined by the initial rate of reaction, $V_0$, and the substrate concentration [S].

In various alternative embodiments, an enzymatic DNA molecule of the present invention has an enhanced or optimized ability to cleave nucleic acid substrates, preferably RNA substrates. In preferred embodiments, the enhanced or optimized ability of an enzymatic DNA molecule to cleave RNA substrates shows about a 10- to $10^9$-fold improvement over the uncatalyzed rate. In more preferred embodiments, an enzymatic DNA molecule of the present invention is able to cleave RNA substrates at a rate that is about $10^3$- to $10^7$-fold improved over "progenitor" species. In even more preferred embodiments, the enhanced or optimized ability to cleave RNA substrates is expressed as a $10^4$- to $10^6$-fold improvement over the progenitor. One skilled in the art will appreciate that the enhanced or optimized ability of an enzymatic DNA molecule to cleave nucleic acid substrates may vary depending upon the selection constraints applied during the in vitro evolution procedure of the invention.

Various preferred methods of modifying deoxyribozymes and other enzymatic DNA molecules and nucleases of the present invention are further described in Examples 1–3 hereinbelow.

C. Nucleotide Analogs

As noted above, the term "nucleotide analog" as used herein generally refers to a purine or pyrimidine nucleotide that differs structurally from A, T, G, C, or U, but is sufficiently similar to substitute for the normal nucleotide in a nucleic acid molecule. As used herein, the term "nucleotide analog" encompasses altered bases, different sugars, altered phosphate backbone, or any combination of these alterations. Examples of nucleotide analogs useful according to the present invention include those listed in the following Table, most of which are found in the approved listing of modified bases at 37 CFR §1.822 (which is incorporated herein by reference).

TABLE 1

Nucleotide Analogs

| Abbreviation | Description |
|---|---|
| ac4c | 4-acetylcytidine |
| chm5u | 5-(carboxyhydroxylmethyl)uridine |
| cm | 2'-O-methylcytidine |
| cmnm5s2u | 5-carboxymethylaminomethyl-2-thiouridine |
| d | dihydrouridine |
| fm | 2'-O-methylpseudouridine |
| galq | β, D-galactosylqueosine |
| gm | 2'-O-methylguanosine |
| i | inosine |
| i6a | N6-isopentenyladenosine |
| m1a | 1-methyladenosine |
| m1f | 1-methylpseudouridine |
| m1g | 1-methylguanosine |
| m1I | 1-methylinosine |
| m22g | 2,2-dimethylguanosine |
| m2a | 2-methyladenosine |
| m2g | 2-methylguanosine |
| m3c | 3-methylcytidine |
| m5c | 5-methylcytidine |
| m6a | N6-methyladenosine |
| m7g | 7-methylguanosine |
| mam5u | 5-methylaminomethyluridine |
| mam5s2u | 5-methoxyaminomethyl-2-thiouridine |
| manq | β, D-mannosylmethyluridine |
| mcm5s2u | 5-methoxycarbonylmethyluridine |
| mo5u | 5-methoxyuridine |
| ms2i6a | 2-methylthio-N6-isopentenyladenosine |
| ms2t6a | N-((9-β-D-ribofuranosyl-2-methylthiopurine-6-yl)carbamoyl)threonine |
| mt6a | N-((9-β-D-ribofuranosylpurine-6-yl)N-methyl-carbamoyl)threonine |
| mv | uridine-5-oxyacetic acid methylester |
| o5u | uridine-5-oxyacetic acid (v) |

TABLE 1-continued

Nucleotide Analogs

| Abbreviation | Description |
| --- | --- |
| osyw | wybutoxosine |
| p | pseudouridine |
| q | queosine |
| s2c | 2-thiocytidine |
| s2t | 5-methyl-2-thiouridine |
| s2u | 2-thiouridine |
| s4u | 4-thiouridine |
| t | 5-methyluridine |
| t6a | N-((9-β-D-ribofuranosylpurine-6-yl)carbamoyl)threonine |
| tm | 2'-O-methyl-5-methyluridine |
| um | 2'-O-methyluridine |
| yw | wybutosine |
| x | 3-(3-amino-3-carboxypropyl)uridine, (acp3)u |
| araU | β, D-arabinosyl |
| araT | β, D-arabinosyl |

Other useful analogs include those described in published international application no. WO 92/20823 (the disclosures of which are incorporated herein by reference), or analogs made according to the methods disclosed therein. Analogs described in DeMesmaeker, et al., *Angew. Chem. Int. Ed. Engl.* 33: 226–229 (1994); DeMesmaeker, et al., *Synlett:* 733–736 (Oct. 1993); Nielsen, et al., *Science* 254: 1497–1500 (1991); and Idziak, et al., *Tetrahedron Letters* 34: 5417–5420 (1993) are also useful according to the within-disclosed invention and said disclosures are incorporated by reference herein.

D. Methods of Engineering Enzymatic DNA Molecules

The present invention also contemplates methods of producing nucleic acid molecules having a predetermined activity. In one preferred embodiment, the nucleic acid molecule is an enzymatic DNA molecule. In another variation, the desired activity is a catalytic activity.

In one embodiment, the present invention contemplates methods of synthesizing enzymatic DNA molecules that may then be "engineered" to catalyze a specific or predetermined reaction. Methods of preparing enzymatic DNA molecules are described herein; see, e.g., Examples 1–3 hereinbelow. In other embodiments, an enzymatic DNA molecule of the present invention may be engineered to bind small molecules or ligands, such as adenosine triphosphate (ATP). (See, e.g., Sassanfar, et al., *Nature* 364: 550–553 (1993).)

In another embodiment, the present invention contemplates that a population of enzymatic DNA molecules may be subjected to mutagenizing conditions to produce a diverse population of mutant enzymatic DNA molecules (which may alternatively be called "deoxyribozymes"). Thereafter, enzymatic DNA molecules having desired characteristics are selected and/or separated from the population and are subsequently amplified.

Alternatively, mutations may be introduced in the enzymatic DNA molecule by altering the length of the recognition domains of the enzymatic DNA molecule. The recognition domains of the enzymatic DNA molecule associate with a complementary sequence of bases within a substrate nucleic acid sequence. Methods of altering the length of the recognition domains are known in the art and include PCR, for example; useful techniques are described further in the Examples below.

Alteration of the length of the recognition domains of an enzymatic DNA molecule may have a desirable effect on the binding specificity of the enzymatic DNA molecule. For example, an increase in the length of the recognition domains may increase binding specificity between the enzymatic DNA molecule and the complementary base sequences of an oligonucleotide in a substrate, or may enhance recognition of a particular sequence in a hybrid substrate. In addition, an increase in the length of the recognition domains may also increase the affinity with which it binds to substrate. In various embodiments, these altered recognition domains in the enzymatic DNA molecule confer increased binding specificity and affinity between the enzymatic DNA molecule and its substrate.

It has recently been noted that certain oligonucleotides are able to recognize and bind molecules other than oligonucleotides with complementary sequences. These oligonucleotides are often given the name "aptamers". For example, Ellington and Szostak describe RNA molecules that are able to bind a variety of organic dyes (*Nature* 346: 818–822 (1990)), while Bock, et al. describe ssDNA molecules that bind human thrombin (*Nature* 355: 564–566 (1992)). Similarly, Jellinek, et al. describe RNA ligands to basic fibroblast growth factor (*PNAS USA* 90: 11227–11231 (1993)). Thus, it is further contemplated herein that the catalytically active DNA enzymes of the present invention may be engineered according to the within-described methods to display a variety of capabilities associated with aptamers.

One of skill in the art should thus appreciate that the enzymatic DNA molecules of this invention can be altered at any nucleotide sequence, such as the recognition domains, by various methods disclosed herein, including PCR and 3SR. For example, additional nucleotides can be added to the 5' end of the enzymatic DNA molecule by including additional nucleotides in the primers.

Enzymatic DNA molecules of the present invention may also be prepared or engineered in a more non-random fashion via use of methods such as site-directed mutagenesis. For example, site-directed mutagenesis may be carried out essentially as described in Morinaga, et al., *Biotechnology* 2: 636 (1984), modified as described herein, for application to deoxyribozymes. Useful methods of engineering enzymatic DNA molecules are further described in the Examples below.

In one disclosed embodiment, an enzymatic DNA molecule of the present invention comprises a conserved core flanked by two substrate binding (or recognition) domains or sequences that interact with the substrate through base-pairing interactions. In various embodiments, the conserved core comprises one or more conserved domains or sequences. In another variation, an enzymatic DNA molecule further comprises a "spacer" region (or sequence) between the regions (or sequences) involved in base pairing. In still another variation, the conserved core is "interrupted" at various intervals by one or more less-conserved variable or "spacer" nucleotides.

In various embodiments, the population of enzymatic DNA molecules is made up of at least 2 different types of deoxyribozyme molecules. For example, in one variation, the molecules have differing sequences. In another variation, the deoxyribozymes are nucleic acid molecules having a nucleic acid sequence defining a recognition domain that is contiguous or adjacent to the 5'-terminus of the nucleotide sequence. In various alternative embodiments, enzymatic DNA molecules of the present invention may further comprise one or more spacer regions located 3'-terminal to the recognition domains, one or more loops located 3'-terminal to the recognition domains and/or spacer regions. In other variations, a deoxyribozyme of the present invention may comprise one or more regions which are capable of hybridizing to other regions of the same molecule. Other characteristics of enzymatic DNA molecules produced according to the presently-disclosed methods are described elsewhere herein.

In other embodiments, mutagenizing conditions include conditions that introduce either defined or random nucleotide substitutions within an enzymatic DNA molecule. Examples of typical mutagenizing conditions include conditions disclosed in other parts of this specification and the methods described by Joyce et al., *Nucl. Acids Res.* 17: 711–722 (1989); Joyce, *Gene* 82: 83–87(1989); and Beaudry and Joyce, *Science* 257: 635–41 (1992).

In still other embodiments, a diverse population of mutant enzymatic nucleic acid molecules of the present invention is one that contains at least 2 nucleic acid molecules that do not have the exact same nucleotide sequence. In other variations, from such a diverse population, an enzymatic DNA molecule or other enzymatic nucleic acid having a predetermined activity is then selected on the basis of its ability to perform the predetermined activity. In various embodiments, the predetermined activity comprises, without limitation, enhanced catalytic activity, decreased $K_M$, enhanced substrate binding ability, altered substrate specificity, and the like.

Other parameters which may be considered aspects of enzyme performance include catalytic activity or capacity, substrate binding ability, enzyme turnover rate, enzyme sensitivity to feedback mechanisms, and the like. In certain aspects, substrate specificity may be considered an aspect of enzyme performance, particularly in situations in which an enzyme is able to recognize and bind two or more competing substrates, each of which affects the enzymes' performance with respect to the other substrate(s).

Substrate specificity, as used herein, may refer to the specificity of an enzymatic nucleic acid molecule as described herein for a particular substrate, such as one comprising ribonucleotides only, deoxyribonucleotides only, or a composite of both. Substrate molecules may also contain nucleotide analogs. In various embodiments, an enzymatic nucleic acid molecule of the present invention may preferentially bind to a particular region of a hybrid or non-hybrid substrate.

The term or parameter identified herein as "substrate specificity" may also include sequence specificity; i.e., an enzymatic nucleic acid molecule of the present invention may "recognize" and bind to a nucleic acid substrate having a particular nucleic acid sequence. For example, if the substrate recognition domains of an enzymatic nucleic acid molecule of the present invention will only bind to substrate molecules having a series of one or two ribonucleotides (e.g., rA) in a row, then the enzymatic nucleic acid molecule will tend not to recognize or bind nucleic acid substrate molecules lacking such a sequence.

With regard to the selection process, in various embodiments, selecting includes any means of physically separating the mutant enzymatic nucleic acids having a predetermined activity from the diverse population of mutant enzymatic nucleic acids. Often, selecting comprises separation by size, by the presence of a catalytic activity, or by hybridizing the mutant nucleic acid to another nucleic acid, to a peptide, or some other molecule that is either in solution or attached to a solid matrix.

In various embodiments, the predetermined activity is such that the mutant enzymatic nucleic acid having the predetermined activity becomes labelled in some fashion by virtue of the activity. For example, the predetermined activity may be an enzymatic DNA molecule activity whereby the activity of the mutant enzymatic nucleic acid upon its substrate causes the mutant enzymatic nucleic acid to become covalently linked to it. The mutant enzymatic nucleic acid is then selected by virtue of the covalent linkage.

In other embodiments, selecting a mutant enzymatic nucleic acid having a predetermined activity includes amplification of the mutant enzymatic nucleic acid (see, e.g., Joyce, *Gene* 82: 83–87 (1989); Beaudry and Joyce, *Science* 257: 635–41 (1992)). Other methods of selecting an enzymatic nucleic acid molecule having a predetermined characteristic or activity are described in the Examples section.

E. Compositions

The invention also contemplates compositions containing one or more types or populations of enzymatic DNA molecules of the present invention; e.g., different types or populations may recognize and cleave different nucleotide sequences. Compositions may further include a ribonucleic acid-containing substrate. Compositions according to the present invention may further comprise lead ion, magnesium ion, or other divalent or monovalent cations, as discussed herein.

Preferably, the enzymatic DNA molecule is present at a concentration of about 0.05 $\mu$M to about 2 $\mu$M. Typically, the enzymatic DNA molecule is present at a concentration ratio of enzymatic DNA molecule to substrate of from about 1:5 to about 1:50. More preferably, the enzymatic DNA molecule is present in the composition at a concentration of about 0.1 $\mu$M to about 1 $\mu$M. Even more preferably, compositions contain the enzymatic DNA molecule at a concentration of about 0.1 $\mu$M to about 0.5 $\mu$M. Preferably, the substrate is present in the composition at a concentration of about 0.5 $\mu$M to about 1000 $\mu$M. One skilled in the art will understand that there are many sources of nucleic acid-containing substrates including naturally-occurring and synthetic sources. Sources of suitable substrates include, without limitation, a variety of viral and retroviral agents, including HIV-1, HIV-2, HTLV-I, and HTLV-II.

Other suitable substrates include, without limitation, viral and retroviral agents including those comprising or produced by picornaviruses, hepadnaviridae (e.g., HBV HCV), papillomaviruses (e.g., HPV), gammaherpesvirinae (e.g., EBV), lymphocryptoviruses, leukemia viruses (e.g., HTLV-I and -II), flaviviruses, togaviruses, herpesviruses (including alphaherpesviruses and betaherpesviruses), cytomegaloviruses (CMV), influenza viruses, and viruses and retroviruses contributing to immunodeficiency diseases and syndromes (e.g., HIV-1 and -2). In addition, suitable substrates include viral and retroviral agents which infect non-human primates, including, without limitation, the simian and feline immunodeficiency viruses and bovine leukemia viruses.

Magnesium ion, lead ion, or another suitable monovalent or divalent cation, as described previously, may also be present in the composition, at a concentration of about 1–100 mM. More preferably, the preselected ion is present in the composition at a concentration of about 2 mM to about 50 mM, with a concentration of about 5 mM being particularly preferred. One skilled in the art will understand that the ion concentration is only constrained by the limits of solubility of it source (e.g. magnesium) in aqueous solution and a desire to have the enzymatic DNA molecule present in the same composition in an active conformation.

The invention also contemplates compositions containing an enzymatic DNA molecule of the present invention, hybrid deoxyribonucleotide-ribonucleotide molecules, and magnesium or lead ion in concentrations as described hereinabove. As noted previously, other monovalent or divalent ions (e.g., $Ca^{2+}$) may be used in place of magnesium.

Also contemplated by the present invention are compositions containing an enzymatic DNA molecule of the present invention, nucleic acid-containing substrate (e.g. RNA), and a preselected ion at a concentration of greater than about 1 millimolar, wherein said substrate is greater in length than the recognition domains present on the enzymatic DNA molecule.

In one variation, a composition comprises an enzymatic DNA molecule-substrate complex, wherein base pairing between an enzymatic DNA molecule and its substrate is contiguous. In another embodiment, base pairing between an enzymatic DNA molecule and its substrate is interrupted by one or more noncomplementary pairs.

In a variety of alternative embodiments, a composition of the present invention may further comprise a monovalent cation, a divalent cation, both, or neither.

In another variation, an enzymatic DNA molecule of the present invention is capable of functioning efficiently in the presence or absence of a divalent cation. In one variation, a divalent cation is present and comprises $Pb^{2+}$, $Mg^{2+}$, $Zn^{2+}$, or $Ca^{2+}$. Alternatively, an enzymatic DNA molecule of the present invention is capable of functioning efficiently in the presence or absence of divalent cations. It is anticipated that cation concentrations similar to those described herein for $Pb^{2+}$ will be useful as disclosed herein.

Optionally, monovalent cations may also be present in addition to, or as "alternatives" for, divalent cations. For example, monovalent cations such as sodium ($Na^+$) or potassium ($K^+$) may be present, either as dissociated ions or in the form of dissociable compounds such as NaCl or KCl.

In one embodiment, the concentration of monovalent cation present in the composition ranges from 0–1.0M. In another embodiment, a monovalent cation is present in a concentration ranging from about 0–200 mM. In other embodiments, monovalent cations are present in a concentration ranging from about 1–100 mM. Alternatively, the concentration of monovalent cations ranges from about 2 mM–50 mM. In still other embodiments, the concentration ranges from about 2 mM–25 mM.

F. Methods of Using Enzymatic DNA Molecules

The methods of using enzymatic DNA molecules as disclosed herein are legion. As discussed previously, molecules capable of cleaving the bonds linking neighboring nucleic acids (e.g., phosphoester bonds) have numerous uses encompassing a wide variety of applications. For example, enzymatic DNA molecules having the within-disclosed capabilities, structures, and/or functions are useful in pharmaceutical and medical products (e.g., for wound debridement, clot dissolution, etc.), as well as in household items (e.g., detergents, dental hygiene products, meat tenderizers). Industrial utility of the within-disclosed compounds, compositions and methods is also contemplated and well within the scope of the present invention.

The present invention also describes useful methods for cleaving any single-stranded, looped, partially or fully double-stranded nucleic acid; the majority of these methods employ the novel enzymatically active nucleic acid molecules of the present invention. In various embodiments, the single-stranded nucleic acid segment or portion of the substrate (or the entire substrate itself) comprises DNA, modified DNA, RNA, modified RNA, or composites thereof. The nucleic acid substrate must only be single-stranded at or near the substrate cleavage sequence so that an enzymatic nucleic acid molecule of the present invention can hybridize to the substrate cleavage sequence by virtue of the enzyme's recognition sequence.

A nucleic acid substrate that can be cleaved by a method of this invention may be chemically synthesized or enzymatically produced, or it may be isolated from various sources such as phages, viruses, prokaryotic cells, or eukaryotic cells, including animal cells, plant cells, eukaryotic cells, yeast cells and bacterial cells. Chemically synthesized single-stranded nucleic acids are commercially available from many sources including, without limitation, Research Genetics (Huntsville, Ala.).

RNA substrates may also be synthesized using an Applied Biosystems (Foster City, Calif.) oligonucleotide synthesizer according to the manufacture's instructions. Single-stranded phages are also sources of nucleic acid substrates. (See, e.g., Messing et al., *PNAS USA* 74: 3642–3646 (1977), and Yanisch-Perron et al., *Gene* 33: 103–119 (1985).) Bacterial cells containing single-stranded phages would also be a ready source of suitable single-stranded nucleic acid.

Single-stranded RNA cleavable by a method of the present invention could be provided by any of the RNA viruses such as the picornaviruses, togaviruses, orthomyxoviruses, paramyxoviruses, rhabdoviruses, coronaviruses, arenaviruses or retroviruses. As noted previously, a wide variety of prokaryotic and eukaryotic cells may also be excellent sources of suitable nucleic acid substrates.

The methods of this invention may be used on single-stranded nucleic acids or single-stranded portions of looped or double-stranded nucleic acids that are present inside a cell, including eucaryotic, procaryotic, plant, animal, yeast or bacterial cells. Under these conditions an enzymatic nucleic acid molecule (e.g., an enzymatic DNA molecule or deoxyribozyme) of the present invention could act as an anti-viral agent or a regulator of gene expression. Examples of such uses of enzymatic DNA molecules of the present invention are described further hereinbelow.

In the majority of methods of the present invention, cleavage of single-stranded nucleic acids occurs at the 3'-terminus of a predetermined base sequence. This predetermined base sequence or substrate cleavage sequence typically contains from 1 to about 10 nucleotides. In other preferred embodiments, an enzymatic DNA molecule of the present invention is able to recognize nucleotides either upstream, or upstream and downstream of the cleavage site. In various embodiments, an enzymatic DNA molecule is able to recognize about 2–10 nucleotides upstream of the cleavage site; in other embodiments, an enzymatic DNA molecule is able to recognize about 2–10 nucleotides upstream and about 2–10 nucleotides downstream of the cleavage site. Other preferred embodiments contemplate an enzymatic DNA molecule that is capable of recognizing a nucleotide sequence up to about 30 nucleotides in length, with a length up to about 20 nucleotides being even more preferred.

The within-disclosed methods allow cleavage at any nucleotide sequence by altering the nucleotide sequence of the recognition domains of the enzymatic DNA molecule. This allows cleavage of single-stranded nucleic acid in the absence of a restriction endonuclease site at that position.

An enzymatic DNA molecule of the present invention may be separated from the remainder of the single-stranded nucleic acid substrate by site-specific hydrolysis at the appropriate cleavage site. Separation of the enzymatic DNA molecule from the substrate allows the enzymatic DNA molecule to carry out another cleavage reaction.

Generally, the nucleic acid substrate is treated under appropriate nucleic acid cleaving conditions—preferably, physiologic conditions—with an effective amount of an enzymatic DNA molecule of the present invention. If the nucleic acid substrate comprises DNA, cleaving conditions may include the presence of a divalent cation at a concentration of about 2–10 mM.

An effective amount of an enzymatic DNA molecule is the amount required to cleave a predetermined base sequence present within the single-stranded RNA. Preferably, the enzymatic DNA molecule is present at a molar ratio of DNA molecule to substrate cleavage sites of 1 to 20. This ratio may vary depending on the length of treating and efficiency of the particular enzymatic DNA molecule under the particular RNA cleavage conditions employed.

Treating typically involves admixing, in aqueous solution, the RNA-containing substrate and the enzyme to form a cleavage admixture, and then maintaining the admixture thus formed under RNA cleaving conditions for a time period sufficient for the enzymatic DNA molecule to cleave the RNA substrate at any of the predetermined nucleotide sequences present in the RNA. In various embodiments, a source of ions is also provided—i.e. monovalent or divalent cations, or both.

In one embodiment of the present invention, the amount of time necessary for the enzymatic DNA molecule to cleave the single-stranded nucleic acid has been predetermined. The amount of time is from about 1 minute to about 24 hours and will vary depending upon the concentration of the reactants, and the temperature of the reaction. Usually, this time period is from about 10 minutes to about 2 hours such that the enzymatic DNA molecule cleaves the single-stranded nucleic acid at any of the predetermined nucleotide sequences present.

The invention further contemplates that the nucleic acid cleaving conditions include the presence of a source of divalent cations (e.g., PbOAc) at a concentration of about 2–100 mM. Typically, the nucleic acid cleaving conditions include divalent cation at a concentration of about 2 mM to about 10 mM, with a concentration of about 5 mM being particularly preferred.

The optimal cationic concentration to include in the nucleic acid cleaving conditions can be easily determined by determining the amount of single-stranded nucleic acid cleaved at a given cation concentration. One skilled in the art will understand that the optimal concentration may vary depending on the particular enzymatic DNA molecule employed.

The present invention further contemplates that the nucleic acid cleaving conditions are at from about pH 6.0 to about pH 9.0. In one preferred embodiment, the pH ranges from about pH 6.5 to pH 8.0. In another preferred embodiment, the pH emulates physiological conditions, i.e., the pH is about 7.0–7.8, with a pH of about 7.5 being particularly preferred.

One skilled in the art will appreciate that the methods of the present invention will work over a wide pH range so long as the pH used for nucleic acid cleaving is such that the enzymatic DNA molecule is able to remain in an active conformation. An enzymatic DNA molecule in an active conformation is easily detected by its ability to cleave single-stranded nucleic acid at a predetermined nucleotide sequence.

In various embodiments, the nucleic acid cleaving conditions also include a variety of temperature ranges; as noted previously, temperature ranges consistent with physiological conditions are especially preferred. In one embodiment, the temperature ranges from about 15° C. to about 60° C. In another variation, the nucleic acid cleaving conditions are from about 30° C. to about 56° C. The temperature of the nucleic acid cleaving conditions are constrained only by the desired cleavage rate and the stability of that particular enzymatic DNA molecule at that particular temperature. In yet another variation, nucleic acid cleavage conditions include a temperature from about 35° C. to about 50° C. In a preferred embodiment, nucleic acid cleavage conditions comprise a temperature range of about 37° C. to about 42° C.

In various methods, the present invention contemplates nucleic acid cleaving conditions including the presence of a polyamine. Polyamines useful for practicing the present invention include spermidine, putrescine, spermine and the like. In one variation, the polyamine is spermidine and it is present at a concentration of about 0.01 mM to about 10 mM. In another variation, the polyamine is present at a concentration of about 1 mM to about 10 mM. Nucleic acid cleavage conditions may also include the presence of polyamine at a concentration of about 2 mM to about 5 mM. In various preferred embodiments, the polyamine is spermidine.

G. Vectors

The present invention also features expression vectors including a nucleic acid segment encoding an enzymatic DNA molecule of the present invention situated within the vector, preferably in a manner which allows expression of that enzymatic DNA molecule within a target cell (e.g., a plant or animal cell).

Thus, in general, a vector according to the present invention preferably includes a plasmid, cosmid, phagemid, virus, or phage vector. Preferably, suitable vectors comprise single-stranded DNA (ssDNA)—e.g., circular phagemid ssDNA. It should also be appreciated that useful vectors according to the present invention need not be circular.

In one variation, nucleotide sequences flanking each of the additional enzymatic DNA molecule-encoding sequences are preferably provided, which sequences may be recognized by the first enzymatic DNA molecule. The intervening or flanking sequences preferably comprise at least 1 nucleotide; more preferably, intervening or flanking sequences are about 2–20 nucleotides in length, with sequences of about 5–10 nucleotides in length being particularly preferred.

The addition of polynucleotide tails may also be useful to protect the 3' end of an enzymatic DNA molecule according to the present invention. These may be provided by attaching a polymeric sequence by employing the enzyme terminal transferase.

A vector according to the present invention includes two or more enzymatic DNA molecules. In one embodiment, a first enzymatic DNA molecule has intramolecular cleaving activity and is able to recognize and cleave nucleotide sequences to release other enzymatic DNA sequences; i.e., it is able to function to "release" other enzymatic DNA molecules from the vector. For example, a vector is preferably constructed so that when the first enzymatic DNA molecule is expressed, that first molecule is able to cleave nucleotide sequences flanking additional nucleotide sequences encoding a second enzymatic DNA molecule, a third enzymatic DNA molecule, and so forth. Presuming said first enzymatic DNA molecule (i.e., the "releasing" molecule) is able to cleave oligonucleotide sequences intramolecularly, the additional (e.g. second, third, and so on) enzymatic DNA molecules (i.e., the "released" molecules) need not possess characteristics identical to the "releasing" molecule. Indeed, in various preferred embodiments, the "released" (i.e. second, third, etc.) enzymatic DNA molecule has amide bond-cleaving activity, while the first ("releasing") enzymatic DNA molecule has nuclease activity.

Alternatively, the first enzymatic DNA molecule may be encoded on a separate vector from the second enzymatic DNA molecule(s) and may have intermolecular cleaving activity. As noted herein, the first enzymatic DNA molecule can be a self-cleaving enzymatic DNA molecule (e.g., a deoxyribozyme), and the second enzymatic DNA molecule may be any desired type of enzymatic DNA molecule (e.g., a deoxyribozyme). When a vector is caused to express RNA from these nucleic acid sequences, that RNA has the ability under appropriate conditions to cleave each of the flanking regions, thereby releasing one or more copies of the second enzymatic DNA molecule. If desired, several different second enzymatic DNA molecules can be placed in the same cell or carrier to produce different deoxyribozymes.

Methods of isolating and purifying enzymatic DNA molecules of the present invention are also contemplated. In addition to the methods described herein, various purification methods (e.g. those using HPLC) and chromatographic isolation techniques are available in the art. See, e.g., the methods described in published international application no. WO 93/23569, the disclosures of which are incorporated herein by reference.

It should also be understood that various combinations of the embodiments described herein are included within the scope of the present invention. Other features and advantages of the present invention will be apparent from the descriptions hereinabove, from the Examples to follow, and from the claims.

EXAMPLES

The following examples illustrate, but do not limit, the present invention.

Example 1

In Vitro Evolution of Enzymatic DNA Molecules: An Overview

In vitro selection and in vitro evolution techniques allow new catalysts to be isolated without a priori knowledge of their composition or structure. Such methods have been used to obtain RNA enzymes with novel catalytic properties. For example, ribozymes that undergo autolytic cleavage with lead cation have been derived from a randomized pool of tRNA$^{Phe}$ molecules (Pan and Uhlenbeck, *Biochemistry* 31: 3887–3895 (1992)). Group I ribozyme variants have been isolated that can cleave DNA (Beaudry and Joyce, *Science* 257: 635–641 (1992)) or that have altered metal dependence (Lehman and Joyce, *Nature* 361: 182–185 (1993)). Starting with a pool of random RNA sequences, molecules have been obtained that catalyze a polymerase-like reaction (Bartel and Szostak, *Science* 261: 1411–1418 (1993)). In the present example, refinement of specific catalytic properties of an evolved enzyme via alteration of the selection constraints during an in vitro evolution procedure is described.

Darwinian evolution requires the repeated operation of three processes: (a) introduction of genetic variation; (b) selection of individuals on the basis of some fitness criterion; and (c) amplification of the selected individuals. Each of these processes can be realized in vitro (Joyce, *Gene* 82: 83 (1989)). A gene can be mutagenized by chemical modification, incorporation of randomized mutagenic oligodeoxynucleotides, or inaccurate copying by a polymerase. (See, e.g., Cadwell and Joyce, in *PCR Methods and Applications* 2: 28–33 (1992); Cadwell and Joyce, *PCR Methods and Applications* 3 (Suppl.): S136–S140 (1994); Chu, et al., *Virology* 98: 168 (1979); Shortle, et al., *Meth. Enzymol.* 100: 457 (1983); Myers, et al., *Science* 229: 242 (1985); Matteucci, et al., *Nucleic Acids Res.* 11: 3113 (1983); Wells, et al., *Gene* 34: 315 (1985); McNeil, et al., *Mol. Cell. Biol.* 5: 3545 (1985); Hutchison, et al., *PNAS USA* 83: 710 (1986); Derbyshire, et al., *Gene* 46: 145 (1986); Zakour, et al., *Nature* 295: 708 (1982); Lehtovaara, et al., *Protein Eng.* 2: 63 (1988); Leung, et al., Technique 1: 11 (1989); Zhou, et al., *Nucl. Acids Res.* 19: 6052 (1991).)

The gene product can be selected, for example, by its ability to bind a ligand or to carry out a chemical reaction. (See, e.g., Joyce, Id. (1989); Robertson and Joyce, *Nature* 344: 467 (1990); Tuerk, et al., *Science* 249: 505 (1990).) The gene that corresponds to the selected gene product can be amplified by a reciprocal primer method, such as the polymerase chain reaction (PCR). (See, e.g., Saiki, et al., *Science* 230: 1350–54 (1985); Saiki, et al., Science 239: 487–491 (1988).)

Alternatively, nucleic acid amplification may be carried out using self-sustained sequence replication (3SR). (See, e.g., Guatelli, et al., *PNAS USA* 87: 1874 (1990), the disclosures of which are incorporated by reference herein.) According to the 3SR method, target nucleic acid sequences may be amplified (replicated) exponentially in vitro under isothermal conditions by using three enzymatic activities essential to retroviral replication: (1) reverse transcriptase, (2) RNase H, and (3) a DNA-dependent RNA polymerase. By mimicking the retroviral strategy of RNA replication by means of cDNA intermediates, this reaction accumulates cDNA and RNA copies of the original target.

In summary, if one is contemplating the evolution of a population of enzymatic DNA molecules, a continuous series of reverse transcription and transcription reactions replicates an RNA target sequence by means of cDNA intermediates. The crucial elements of this design are (a) the oligonucleotide primers both specify the target and contain 5' extensions encoding the T7 RNA polymerase binding site, so that the resultant cDNAs are competent transcription templates; (b) cDNA synthesis can proceed to completion of both strands due to the degradation of template RNA in the intermediate RNA-DNA hybrid by RNase H; and (c) the reaction products (cDNA and RNA) can function as templates for subsequent steps, enabling exponential replication.

If one is evolving enzymatic DNA molecules, various critical elements of this design are somewhat different, as disclosed in these Examples. For instance, (1) the oligonucleotide primers specify the target and are preferably "marked" or labeled in some fashion—e.g., via biotinylation—so the resultant competent template strands are easily identified; and (2) the in vitro selection procedure used preferably depends upon the identification of the most favorable release mechanism.

A major obstacle to realizing Darwinian evolution in vitro is the need to integrate mutation and amplification, both of which are genotype-related, with selection, which is phenotype-related. In the case of nucleic acid enzymes, for which genotype and phenotype are embodied in the same molecule, the task is simplified.

A. Design of Enzymatic DNA Molecules

It is well known that single-stranded DNA can assume interesting tertiary structures. The structure of a "tDNA", for example, closely resembles that of the corresponding tRNA. (See Paquette, et al., *Eur. J. Biochem.* 189: 259–265 (1990).) Furthermore, it has been possible to replace as many as 31 of 35 ribonucleotides within a hammerhead ribozyme, while retaining at least some catalytic activity. (See Perreault, et al., *Nature* 344: 565–567 (1990); Williams, et al., *Proc. Natl. Acad. Sci. USA* 89: 918–921 (1992); Yang, et al., *Biochemistry* 31: 5005–5009 (1992).

In vitro selection techniques have been applied to large populations of random-sequence DNAs, leading to the recovery of specific DNA "aptamers" that bind a target ligand with high affinity (Bock, et al., *Nature* 355: 564–566 (1992); Ellington & Szostak, *Nature* 355: 850–852 (1992); Wyatt & Ecker, *PNAS USA* 91: 1356–1360 (1994)). Recently, two groups carried out the first NMR structural determination of an aptamer, a 15mer DNA that forms a G-quartet structure and binds the protein thrombin with high affinity (Wang, et al., *Biochemistry* 32: 1899–1904 (1993); Macaya, et al., *PNAS USA* 90: 3745–3749 (1993)). These findings were corroborated by an X-ray crystallographic analysis (Padmanabhan, et al., *J. Biol. Chem.* 268: 17651–17654 (1993)).

The ability to bind a substrate molecule with high affinity and specificity is a prerequisite of a good enzyme. In addition, an enzyme must make use of well-positioned functional groups, either within itself or a cofactor, to promote a particular chemical transformation. Furthermore, the enzyme must remain unchanged over the course of the reaction and be capable of operating with catalytic turnover. Some would add the requirement that it be an informational macromolecule, comprised of subunits whose specific ordering is responsible for catalytic activity. While these criteria are open to debate on both semantic and chemical grounds, they serve to distinguish phenomena of chemical rate enhancement that range from simple solvent effects to biological enzymes operating at the limit of substrate diffusion (Albery & Knowles, *Biochemistry* 15: 5631–5640 (1976)).

As described in greater detail hereinbelow, we sought to develop a general method for rapidly obtaining DNA catalysts and DNA enzymes, starting from random sequences. As an initial target, we chose a reaction that we felt was well within the capability of DNA: the hydrolytic cleavage of an RNA phosphodiester, assisted by a divalent metal cofactor. This is the same reaction that is carried out by a variety of naturally-occurring RNA enzymes, including the hammerhead and hairpin motifs. (See, e.g., Forster A. C. & Symons R. H., *Cell* 49: 211–220 (1987); Uhlenbeck, *Nature* 328: 596–600 (1987); Hampel & Tritz, *Biochemistry* 28: 4929–4933 (1989)).

It has recently been shown that, beginning with a randomized library of tRNA molecules, one can obtain ribozymes that have $Pb^{2+}$-dependent, site-specific RNA phosphoesterase activity at neutral pH (Pan & Uhlenbeck, *Biochemistry* 31: 3887–3895 (1992); Pan & Uhlenbeck, *Nature* 358: 560–563 (1992)). This is analogous to the fortuitous self-cleavage reaction of yeast $tRNA^{Phe}$ (Dirheimer & Werner, *Biochimie* 54: 127–144 (1972)), which depends on specific coordination of a $Pb^{2+}$ ion at a defined site within the tRNA. (See Rubin & Sundaralingam, *J. Biomol. Struct. Dyn.* 1: 639–646 (1983); Brown, et al., *Biochemistry* 24: 4785–4801 (1985).) As disclosed herein, our goals included the development of DNAs that could carry out $Pb^{2+}$-dependent cleavage of a particular RNA phosphoester, initially presented within a short leader sequence attached to the 5' end of the DNA, and ultimately located within a separate molecule that could be cleaved in an intermolecular fashion with rapid catalytic turnover. These goals were successfully achieved, as described further below.

No assumptions were made as to how the DNA would interact with the target phosphoester and surrounding nucleotides. Beginning with a pool of approximately $10^{14}$ random 50mer sequences, in vitro selection was allowed to run its course. After five rounds of selection carried out over four days, the population as a whole had attained the ability to cleave the target phosphoester in the presence of 1 mM $Pb^{2+}$ at a rate of about 0.2 $min^{-1}$. This is an approximately $10^5$-fold increase compared to the spontaneous rate of cleavage under the same reaction conditions.

Individuals were isolated from the population, sequenced, and assayed for catalytic activity. Based on this information, the reaction was converted to an intermolecular format and then simplified to allow site-specific cleavage of a 19mer substrate by a 38mer DNA enzyme, in a reaction that proceeds with a turnover rate of 1 $min^{-1}$ at 23° C. and pH 7.0 in the presence of 1 mM PbOAc.

B. In Vitro Selection Scheme

Figure 1:
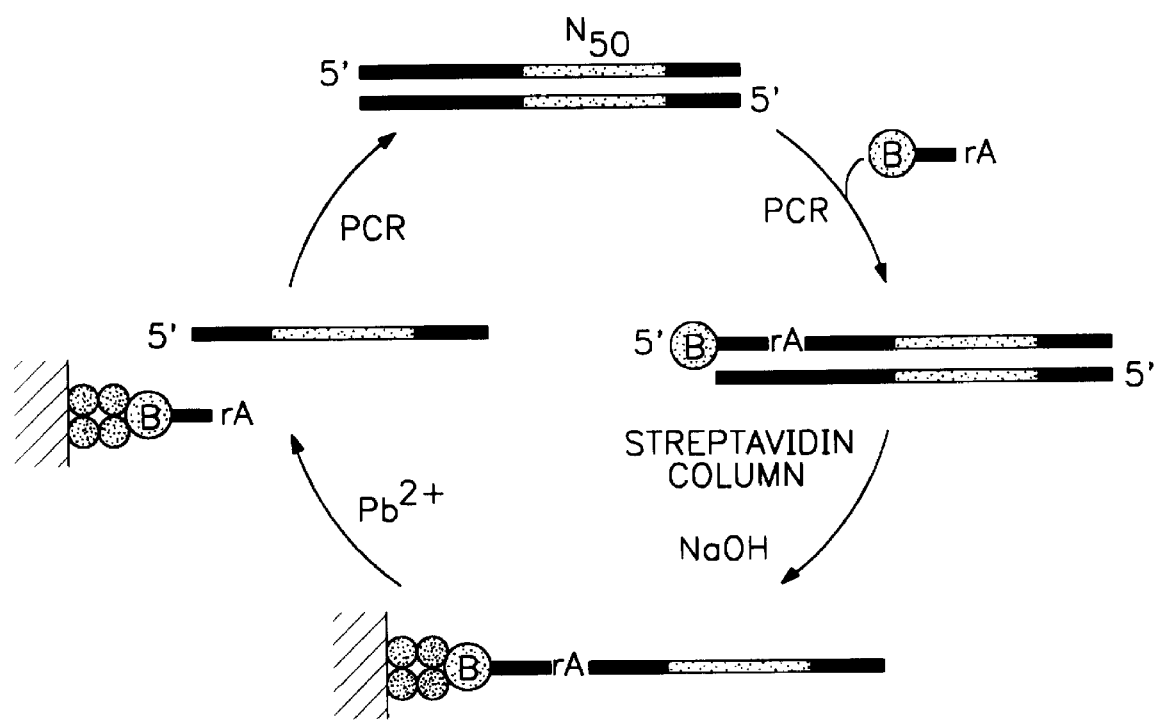
FIG. 1 illustrates a selective amplification scheme for isolation of DNAs that cleave a target RNA phosphoester. As shown, double-stranded DNA that contains a stretch of 50 random nucleotides (the molecule with "$N_{50}$" indicated above it) is amplified by PCR, employing a 5'-biotinylated DNA primer that is terminated at the 3'end by an adenosine ribonucleotide (rA). (The biotin label is indicated via the encircled letter "B".) This primer is extended by Taq polymerase to yield a DNA product that contains a single embedded ribonucleotide. The resulting double-stranded DNA is immobilized on a streptavidin matrix and the unbiotinylated DNA strand is removed by washing with 0.2N NaOH. After re-equilibrating the column with a buffered solution, the column is washed with the same solution with added 1 mM PbOAc. DNAs that undergo $Pb^{2+}$-dependent self-cleavage are released from the column, collected in the eluant, and amplified by PCR. The PCR products are then used to initiate the next round of selective amplification.

A starting pool of approximately $10^{14}$ single-stranded DNA molecules was generated, all of which contain a 5' biotin moiety, followed successively by a fixed domain that includes a single ribonucleotide, a potential catalytic domain comprised of 50 random deoxyribonucleotides, and a second fixed domain that lay at the 3' terminus (FIG. 1).

The pool was constructed by a nested PCR (polymerase chain reaction) technique, beginning with synthetic DNA that contained 50 random nucleotides flanked by primer binding sites. The nested PCR primer was a 5'-biotinylated synthetic oligodeoxynucleotide with a 3'-terminal adenosine ribonucleotide. Ribonucleotide-terminated oligonucleotides efficiently prime template-directed elongation in the context of the PCR (L. E. Orgel, personal communication), in this case giving rise to an extension product that contains a single embedded ribonucleotide.

FIG. 1 illustrates a selective amplification scheme for isolation of DNAs that cleave a target RNA phosphoester. Double-stranded DNA containing a stretch of 50 random nucleotides is amplified via PCR, employing a 5'-biotinylated DNA primer (e.g., primer 3—3a or 3b) terminated at the 3' end by an adenosine ribonucleotide (represented by the symbol "N" or "rA", wherein both N and rA represent an adenosine ribonucleotide). This primer is extended by Taq polymerase to yield a DNA product that contains a single embedded ribonucleotide. The resulting double-stranded DNA is immobilized on a streptavidin matrix and the unbiotinylated DNA strand is removed by washing with 0.2N NaOH. After re-equilibrating the column with a buffered solution, the column is washed with the same solution with added 1 mM PbOAc. DNAs that undergo $Pb^{2+}$-dependent self-cleavage are released from the column, collected in the eluant, and amplified by PCR. The PCR products are then used to initiate the next round of selective amplification.

The PCR products were passed over a streptavidin affinity matrix, resulting in noncovalent attachment of the 5'-biotinylated strand of the duplex DNA. The nonbiotinylated strand was removed by brief washing with 0.2N NaOH, and the bound strand was equilibrated in a buffer containing 0.5M NaCl, 0.5M KCl, 50 mM $MgCl_2$, and 50 mM HEPES (pH 7.0) at 23° C. Next, 1 mM PbOAc was provided in the same buffer, allowing $Pb^{2+}$-dependent cleavage to occur at the target phosphoester, thereby releasing a subset of the DNAs from the streptavidin matrix. In principle, an individual DNA might facilitate its own release by various means, such as disruption of the interaction between biotin and streptavidin or cleavage of one of the deoxyribonucleotide linkages. It was felt that cleavage of the ribonucleoside 3'-O-P bond would be the most likely mechanism for release, based on the relative lability of this linkage, and that $Pb^{2+}$-dependent hydrolytic cleavage would allow release to occur most rapidly. In principle, however, the in vitro selection procedure should identify the most favorable release mechanism as well as those individuals best able to carry out that mechanism.

DNA molecules released from the matrix upon addition of $Pb^{2+}$ were collected in the eluant, concentrated by precipitation with ethanol, and subjected to nested PCR amplification. As in the construction of the starting pool of molecules, the first PCR amplification utilized primers that flank the random region (primers 1 and 2) and the second utilized a 5'-biotinylated primer (primer 3b) that has a 3'-terminal riboadenylate, thereby reintroducing the target RNA phosphoester. The entire selective amplification procedure requires 3–4 hours to perform.

The molecules are purified in three ways during each round of this procedure: first, following PCR amplification, by extracting twice with phenol and once with chloroform/isoamyl alcohol, then precipitating with ethanol; second, following attachment of the DNA to streptavidin, by washing away all the nonbiotinylated molecules under strongly denaturing conditions; and third, following elution with $Pb^{2+}$, by precipitating with ethanol. There is no gel electrophoresis purification step, and thus no selection pressure constraining the molecules to a particular length.

C. Selection of Catalytic DNA

We carried out five successive rounds of in vitro selection, progressively decreasing the reaction time following addition of $Pb^{2+}$ in order to progressively increase the stringency of selection. During rounds 1 through 3, the reaction time was 1 hour; during round 4, it was 20 minutes; and during round 5, it was 1 minute. The starting pool of single-stranded DNAs, together with the population of molecules obtained after each round of selection, was assayed for self-cleavage activity under conditions identical to those employed during in vitro selection (see FIG. 2).

For this assay, the molecules were prepared with a 5'-$^{32}$p rather than a 5'-biotin moiety, allowing detection of both the starting material and the 5' cleavage product. Following a 5-minute incubation, there was no detectable activity in the initial pool (G0) or in the population obtained after the first and second rounds of selection. DNAs obtained after the third round (G3) exhibited a modest level of activity and this activity increased steadily, reaching approximately 50% self-cleavage for the DNAs obtained after the fifth round of selection (G5). Cleavage was detected only at the target phosphoester, even after long incubation times. This activity was lost if $Pb^{2+}$ was omitted from the reaction mixture.

Figure 2:
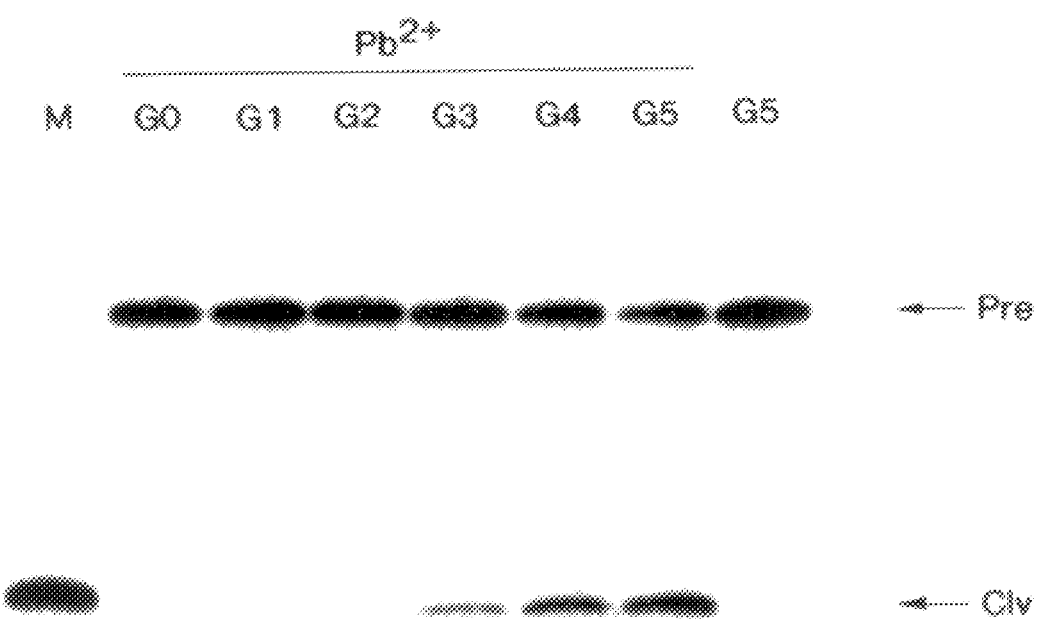
FIG. 2 illustrates self-cleavage activity of the starting pool of DNA (G0) and populations obtained after the first through fifth rounds of selection (G1–G5), in the presence of lead cation ($Pb^{2+}$). The symbol Pre represents 108-nucleotide precursor DNA (SEQ ID NO 4); Clv, 28-nucleotide 5'-cleavage product (SEQ ID NO 5); and M, primer 3a (SEQ ID NO 6), which corresponds in length to the 5'-cleavage product.

FIG. 2 illustrates the self-cleavage activity of the starting pool of DNA (G0) and populations obtained after the first through fifth rounds of selection (G1–G5). Reaction mixtures contained 50 mM $MgCl_2$, 0.5M NaCl, 0.5M KCl, 50 mM HEPES (pH 7.0 at 23° C.), and 3 nM [5'-$^{32}$P]-labeled DNA, incubated at 23° C. for 5 min in either the presence or absence of 1 mM PbOAc. The symbol Pre represents 108-nucleotide precursor DNA (SEQ ID NO 4); Clv, 28-nucleotide 5'-cleavage product (SEQ ID NO 5); and M, primer 3a (SEQ ID NO 6), corresponding in length to the 5'-cleavage product.

The 28-nucleotide 5' cleavage product (Clv) illustrated preferably has the sequence 5'-GGGACGAATTCTAATACGACTCACTATN-3', wherein "N" represents adenosine ribonucleotide with an additional 2', 3'-cyclic phosphate on the 3' end (SEQ ID NO 5). In alternative embodiments, "N" represents adenosine ribonucleotide with an additional 2' or 3' phosphate on the 3' end of the molecule.

In FIG. 2, the "G0" lane "Pre" band comprises a sampling of 108-nucleotide precursor DNAs that each include 50 random nucleotides. Therefore, any given "Pre" sampling will contain a wide variety of precursor DNAs, and each sampling will likely differ from previous and subsequent samplings. The "G1" through "G5" lanes contain "Pre" bands that are increasingly enriched for catalytic DNA molecules, but still contain a large number of different DNA sequences (i.e., differing in the 50 nucleotide randomized domain). A sample of these different sequences from "G5 Pre" DNA is provided in FIG. 3.

Figure 3:
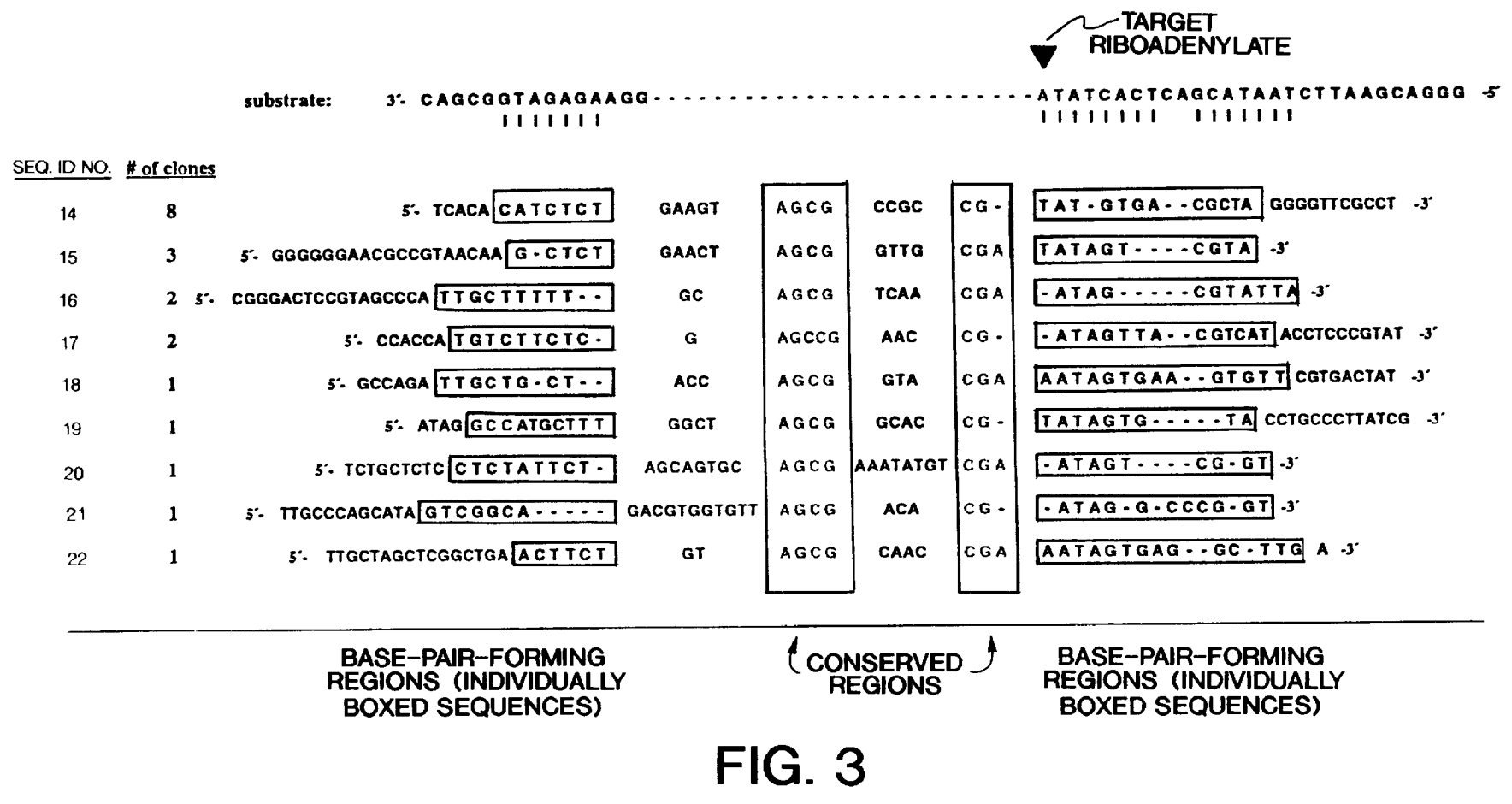

Shotgun cloning techniques were employed to isolate individuals from the G5 population; the complete nucleotide sequences of 20 of these subclones were then determined (see FIG. 3). (Also see, e.g., Cadwell and Joyce, in *PCR Methods and Applications* 2: 28–33 (1992); Cadwell and Joyce, *PCR Methods and Applications* 3 (Suppl.): S136–S140 (1994).) Of the 20 sequences, five were unique, two occurred twice, one occurred three times, and one occurred eight times. All of the individual variants share common sequence elements within the 50-nucleotide region that had been randomized in the starting pool of DNA. They all contain two presumed template regions, one with complementarity to a stretch of nucleotides that lies just upstream from the cleavage site and the other with complementarity to nucleotides that lie at least four nucleotides downstream. Between these two presumed template regions lies a variable domain of 1–11 nucleotides, followed by the fixed sequence 5'-AGCG-3', then a second variable domain of 3–8 nucleotides, and finally the fixed sequence 5'-CG-3' or 5'-CGA-3'. Nucleotides that lie outside of the two presumed template regions are highly variable in both sequence and length. In all of the sequenced subclones, the region corresponding to the 50 initially-randomized nucleotides remains a total of 50 nucleotides in length.

FIG. 3 illustrates the sequence alignment of individual variants isolated from the population after five rounds of selection. The fixed substrate domain (5'-GGGACGAATTCTAATACGACTCACTATrAGGAAGAG ATGGCGAC-3', or 5'-GGGACGAATTCTAATACGACT CACTATNGGAAGAGATGGCGAC-3', where N represents adenosine ribonucleotide) (SEQ ID NO 13) is shown at the top, with the target riboadenylate identified with an inverted triangle. Substrate nucleotides that are commonly involved in presumed base-pairing interactions are indicated by a vertical bar. Sequences corresponding to the 50 initially-randomized nucleotides are aligned antiparallel to the substrate domain. All of the variants are 3'-terminated by the fixed sequence 5'-CGGTAAGCTTGGCAC-3'(SEQ ID NO 1) ("primer site"; not shown). Nucleotides within the initially-randomized region that are presumed to form base pairs with the substrate domain are indicated on the right and left sides of the Figure; the putative base-pair-forming (or substrate binding) regions of the enzymatic DNA molecules are individually boxed in each sequence shown. The highly-conserved nucleotides within the putative catalytic domain are illustrated in the two boxed columns.

While it is anticipated that additional data will be helpful in constructing a meaningful secondary structural model of the catalytic domain, we note that, like the hammerhead and hairpin ribozymes, the catalytic domain of our enzymatic DNA molecules appears to contain a conserved core flanked by two substrate binding regions (or recognition domains) that interact with the substrate through base-pairing interactions. Similar to the hammerhead and hairpin ribozymes, the catalytic DNAs also appear to require a short stretch of unpaired substrate nucleotides—in this case 5'-GGA-3'—between the two regions that are involved in base pairing.

It was also interesting to note that each of the nine distinct variants exhibited a different pattern of presumed complementarity with the substrate domain. In some cases, base pairing was contiguous, while in others it was interrupted by one or more noncomplementary pairs. The general tendency seems to be to form tighter interaction with the nucleotides that lie upstream from the cleavage site compared to those that lie downstream. Binding studies and site-directed mutagenesis analysis should enable us to gain further insights and to further substantiate this conjecture.

In order to gain further insight into the sequence requirements for catalytic function, the self-cleavage activity of six of the nine variants was tested and evaluated under the within-described selection conditions (see FIG. 3). Not surprisingly, the sequence that occurred in eight of the 20 subclones proved to be the most reactive, with a first-order rate constant of 1.4 min$^{-1}$. All of the studied variants were active in the self-cleavage assay and all gave rise to a single 5'-labeled product corresponding to cleavage at the target RNA phosphoester.

The dominant subclone was further analyzed under a variety of reaction conditions. Its self-cleavage activity was dependent on Pb$^{2+}$ but was unaffected if Mg$^{2+}$ was omitted from the reaction mixture. There was a requirement for a monovalent cation as well, which can be met by either Na$^+$ or K$^+$. The reaction rate increased linearly with increasing concentration of monovalent cation over the range of 0–1.0M (r=0.998). Other variables that might affect the reaction, such as pH, temperature, and the presence of other divalent metals, are in the process of being evaluated.

Example 2

Materials and Methods

A. Oligonucleotides and Oligonucleotide Analogues

Synthetic DNAs and DNA analogues were purchased from Operon Technologies. The 19-nucleotide substrate, 5'-pTCACTATrAGGAAGAGATGG-3' (or 5'-pTCACTATNGGAAGAGATGG-3', wherein "N" represents adenosine ribonucleotide) (SEQ ID NO 7), was prepared by reverse-transcriptase catalyzed extension of 5'-pTCACTATrA-3' (or 5'-pTCACTATN-3', wherein "N" represents adenosine ribonucleotide) (SEQ ID NO 8), as previously described (Breaker, Banerji, & Joyce, *Biochemistry* 33: 11980–11986 (1994)), using the template 5'-CCATCTCTTCCTATAGTGAGTCCGGCTGCA-3', (SEQ ID NO 9). Primer 3, 5'-GGGACGAATTCTAATACGACTCACTATrA-3' (or 5'-GGGACGAATTCTAATACGACTCACTATN-3', wherein "N" represents adenosine ribonucleotide) (SEQ ID NO 6), was either 5'-labeled with [γ-$^{32}$P]ATP and T4 polynucleotide kinase (primer 3a) or 5'-thiophosphorylated with [γ-S]ATP and T4 polynucleotide kinase and subsequently biotinylated with N-iodoacetyl-N'-biotinylhexylenediamine (primer 3b).

B. DNA Pool Preparation

The starting pool of DNA was prepared by PCR using the synthetic oligomer 5'-GTGCCAAGCTTACCG-N$_{50}$-GTCGCCATCTCTTCC-3' (SEQ ID NO 4), where N is an equimolar mixture of G, A, T and C. A 2-ml PCR, containing 500 pmoles of the randomized oligomer, 1,000 pmoles primer 1 (5'-GTGCCAAGCTTACCG-3', SEQ ID NO 10), 500 pmoles primer 2 (5'-CTGCAGAATTCTAAT ACGACTCACTATAGGAAGAGATGGCGAC-3', SEQ ID NO 11), 500 pmoles primer 3b, 10 μCi [α-$^{32}$P]dATP, and 0.2 U μl$^{-1}$ Taq DNA polymerase, was incubated in the presence of 50 mM KCl, 1.5 mM MgCl$_2$, 10 mM Tris-HCl (pH 8.3 at 23° C.), 0.01% gelatin, and 0.2 mM of each dNTP for 1 min at 92° C., 1 min at 50° C., and 2 min at 72° C., then 5 cycles of 1 min at 92° C., 1 min at 50° C., and 1 min at 72° C. The resulting mixture was extracted twice with phenol and once with chloroform/isoamyl alcohol, and the DNA was isolated by precipitation with ethanol.

C. In Vitro Selection

The starting pool of DNA was resuspended in 500 μL of buffer A (1M NaCl and 50 mM HEPES (pH 7.0 at 23° C.)) and was passed repeatedly over a streptavidin column (AffiniTip Strep 20, Genosys, The Woodlands, Tex.). The column was washed with five 100-μl volumes of buffer A, followed by five 100-μl volumes of 0.2N NaOH, then equilibrated with five 100-μl volumes of buffer B (0.5M NaCl, 0.5M KCl, 50 mM MgCl$_2$, and 50 mM HEPES (pH 7.0 at 23° C.)). The immobilized single-stranded DNA was eluted over the course of 1 hr with three 20-μl volumes of buffer B with added 1 mM PbOAc. The entire immobilization and elution process was conducted at 23° C. The eluant was collected in an equal volume of buffer C (50 mM HEPES (pH 7.0 at 23° C.) and 80 mM EDTA) and the DNA was precipitated with ethanol.

The resulting DNA was amplified in a 100-μL PCR containing 20 pmoles primer 1, 20 pmoles primer 2, 0.05 U μl$^{-1}$ Taq polymerase, 50 mM KCl, 1.5 mM MgCl$_2$, 10 mM Tris-HCl (pH 8.3 at 23° C.), 0.01% gelatin, and 0.2 mM of each dNTP for 30 cycles of 10 sec at 92° C., 30 sec at 50° C., and 30 sec at 72° C. The reaction products were extracted twice with phenol and once with chloroform/isoamyl alcohol, and the DNA was recovered by precipitation with ethanol. Approximately 4 pmoles of the amplified DNA was added to a second, nested PCR containing 100 pmoles primer 1, 100 pmoles primer 3b, 20 μCi [α-$^{32}$P]dATP, and 0.1 U μl$^{-1}$ Taq polymerase, in a total volume of 200 μL that was amplified for 10 cycles of 1 min at 92° C., 1 min at 50° C., and 1 min at 72° C. The PCR products were once more extracted and precipitated, and the resulting DNA was resuspended in 50 μL buffer A, then used to begin the next round of selection.

The second and third rounds were carried out as above, except that the nested PCR at the end of the third round was performed in a 100-μl volume. During the fourth round, the elution time following addition of Pb$^{2+}$ was reduced to 20 min (two 20-μL elution volumes) and only half of the recovered DNA was used in the first PCR, which involved only 15 temperature cycles. During the fifth round, the elution time was reduced to 1 min (two 20-μL elution volumes) and only one-fourth of the recovered DNA was used in the first PCR, which involved 15 temperature cycles. DNA obtained after the fifth round of selection was subcloned and sequenced, as described previously (Tsang & Joyce, *Biochemistry* 33: 5966–5973 (1994)).

D. Kinetic Analysis of Catalytic DNAs

Populations of DNA and various subcloned individuals were prepared with a 5'$^{32}$P label by asymmetric PCR in a 25-μl reaction mixture containing 10 pmoles primer 3a, 0.5 pmoles input DNA, and 0.1 U μl$^{-1}$ Taq polymerase, under conditions as described above, for 10 cycles of 1 min at 92° C., 1 min at 50° C., and 1 min at 72° C. The resulting

[5'-$^{32}$P]-labeled amplification products were purified by electrophoresis in a 10% polyacrylamide/8M gel.

Self-cleavage assays were carried out following preincubation of the DNA in buffer B for 10 min. Reactions were initiated by addition of PbOAc to 1 mM final concentration and were terminated by addition of an equal volume of buffer C. Reaction products were separated by electrophoresis in a 10% polyacrylamide/8M gel. Kinetic assays under multiple-turnover conditions were carried out in buffer B that included 50 μg ml.$^{-1}$ BSA to prevent adherence of material to the vessel walls. Substrate and enzyme molecules were preincubated separately for 5 min in reaction buffer that lacked Pb$^{2+}$, then combined, and the reaction was initiated by addition of PbOAc to a final concentration of 1 mM.

Example 3

Evolution of Deoxyribozymes That Cleave Intermolecularly

A. Conversion to an Intermolecular Format

Based on the variable pattern of presumed base-pairing interactions between the catalytic and substrate domains of the studied variants, it was felt that it would be reasonably straightforward to convert the DNA-catalyzed reaction to an intermolecular format. In doing so, we wished to simplify the two substrate-binding regions of the catalyst so that each would form an uninterrupted stretch of 7–8 base pairs with the substrate. In addition, we wished to provide a minimal substrate, limited to the two base-pairing regions and the intervening sequence 5'-GGA-3' (FIG. 4A).

Figure 4A:
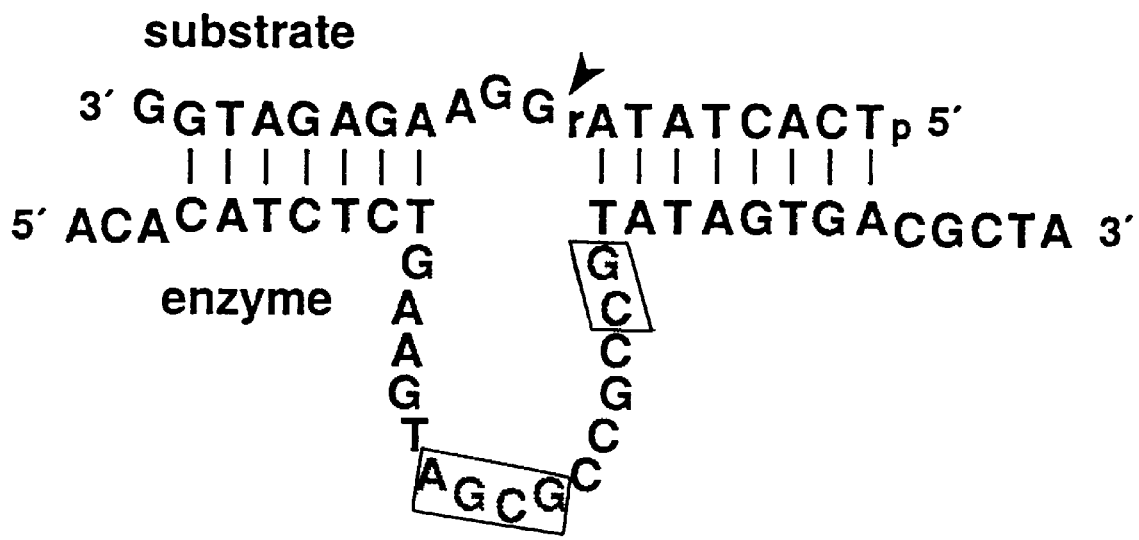
FIGS. 4A and 4B illustrate DNA-catalyzed cleavage of an RNA phosphoester in an intermolecular reaction that proceeds with catalytic turnover.
Figure 4B:
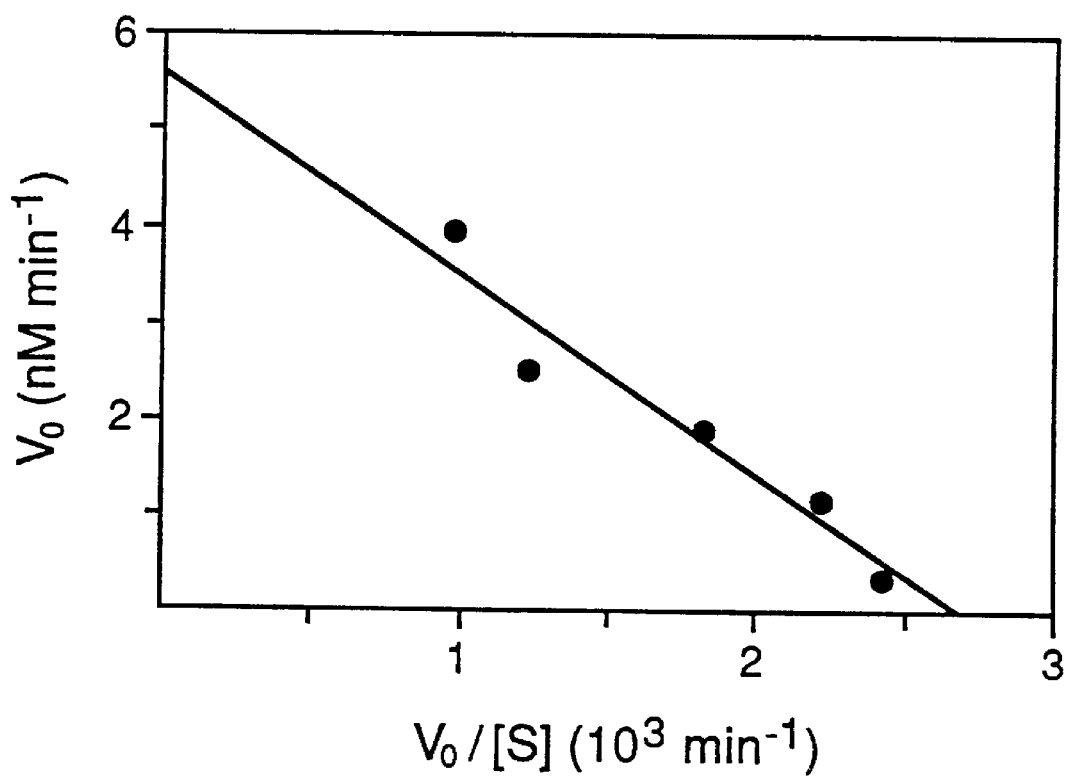

FIGS. 4A and 4B illustrate DNA-catalyzed cleavage of an RNA phosphoester in an intermolecular reaction that proceeds with catalytic turnover. FIG. 4A is a diagrammatic representation of the complex formed between the 19mer substrate and 38mer DNA enzyme. The substrate contains a single adenosine ribonucleotide ("rA" or "N", adjacent to the arrow), flanked by deoxyribonucleotides. The synthetic DNA enzyme is a 38-nucleotide portion of the most frequently occurring variant shown in FIG. 3. Highly-conserved nucleotides located within the putative catalytic domain are "boxed". As illustrated, one conserved sequence is "AGCG", while another is "CG" (reading in the 5'→3' direction).

FIG. 4B shows an Eadie-Hofstee plot used to determine $K_m$ (negative slope) and $V_{max}$ (y-intercept) for DNA-catalyzed cleavage of [5'-$^{32}$P]-labeled substrate under conditions identical to those employed during in vitro selection. Initial rates of cleavage were determined for reactions involving 5 nM DNA enzyme and either 0.125, 0.5, 1, 2, or 4 μM substrate.

In designing the catalytic domain, we relied heavily on the composition of the most reactive variant, truncating by two nucleotides at the 5' end and 11 nucleotides at the 3' end. The 15 nucleotides that lay between the two template regions were left unchanged and a single nucleotide was inserted into the 3' template region to form a continuous stretch of nucleotides capable of forming base pairs with the substrate. The substrate was simplified to the sequence 5'-TCACTATrA·GGAAGAGATGG-3'(or 5'-TCACTATN·GGAAGAGATGG-3', wherein "N" represents adenosine ribonucleotide) (SEQ ID NO 12), where the underlined nucleotides correspond to the two regions involved in base pairing with the catalytic DNA molecule.

The simplified reaction system, employing a 38mer catalytic DNA molecule (catalyst) comprised entirely of deoxyribonucleotides and a 19mer substrate containing a single ribonucleotide embedded within an otherwise all-DNA sequence, allows efficient DNA-catalyzed phosphoester cleavage with rapid turnover. Over a 90-minute incubation in the presence of 0.01 μM catalyst and 1 μM substrate, 46% of the substrate is cleaved, corresponding to 46 turnovers of the catalyst. A preliminary kinetic analysis of this reaction was carried out, evaluated under multiple-turnover conditions. The DNA catalyst exhibits Michaelis-Menten kinetics, with values for $k_{cat}$ and $K_m$ of 1 min$^{-1}$ and 2 μM, respectively (see FIG. 4B). The value for $K_m$ is considerably greater than the expected dissociation constant between catalyst and substrate based on Watson-Crick interactions. The substrate was incubated under identical reaction conditions (but in the absence of the catalyst); a value for $k_{uncat}$ of 4×10$^{-6}$ min$^{-1}$ was obtained. This is consistent with the reported value of 5×10$^{-3}$ min$^{-1}$ for hydrolysis of the more labile 1-nitrophenyl-1,2-propanediol in the presence of 0.5 mM Pb$^{2+}$ at pH 7.0 and 37° C. (Breslow & Huang, *PNAS USA* 88: 4080–4083 (1991)).

It is now presumed that the phosphoester cleavage reaction proceeds via a hydrolytic mechanism involving attack by the ribonucleoside 2'-hydroxyl on the vicinal phosphate, generating a 5' product with a terminal 2'(3')-cyclic phosphate and 3' product with a terminal 5'-hydroxyl. In support of this mechanism, the 3'-cleavage product is efficiently phosphorylated with T4 polynucleotide kinase and [γ-$^{32}$P] ATP, consistent with the availability of a free 5'-hydroxyl (data not shown).

B. Discussion

After five rounds of in vitro selection, a population of single-stranded DNA molecules that catalyze efficient Pb$^{2+}$-dependent cleavage of a target RNA phosphoester was obtained. Based on the common features of representative individuals isolated from this population, a simplified version of both the catalytic and substrate domains was constructed, leading to a demonstration of rapid catalytic turnover in an intermolecular context. Thus the 38mer catalytic domain provides an example of a DNA enzyme, or what might be termed a "deoxyribozyme".

Referring to this molecule as an enzyme, based on the fact that it is an informational macromolecule capable of accelerating a chemical transformation in a reaction that proceeds with rapid turnover and obeys Michaelis-Menten kinetics, may not satisfy everyone's notion of what constitutes an enzyme. Some might insist that an enzyme, by definition, must be a polypeptide. If, however, one accepts the notion of an RNA enzyme, then it seems reasonable to adopt a similar view concerning DNA enzymes. Considering how quickly we were able to generate this molecule from a pool of random-sequence DNAs, we expect that many other examples of synthetic DNA enzymes will appear in the near future.

The Pb$^{2+}$-dependent cleavage of an RNA phosphoester was chosen as an initial target for DNA catalysis because it is a straightforward reaction that simply requires the proper positioning of a coordinated Pb$^{2+}$-hydroxyl to facilitate deprotonation of the 2' hydroxyl that lies adjacent to the cleavage site. (See, e.g., Pan, et al., in *The RNA World*, Gesteland & Atkins (eds.), pp. 271–302, Cold Spring Harbor Laboratory Press, Cold Spring Harbor, N.Y. (1993).) Pb$^{2+}$ is known to coordinate to the N7 position of purines, the O6 position of guanine, the O4 position of uracil, and the N3 position of cytosine (Brown, et al., *Nature* 303: 543–546 (1993)). Thus, the differences in sugar composition and conformation of DNA compared to RNA seemed unlikely to prevent DNA from forming a well-defined Pb$^{2+}$-binding pocket.

A substrate that contains a single ribonucleotide within an otherwise all-DNA sequence was chosen because it provided a uniquely favored site for cleavage and insured that any resulting catalytic activity would be attributable solely to DNA. Substrate recognition appears to depend on two regions of base-pairing interactions between the catalyst and substrate. However, the unpaired substrate nucleotides, 5'-GGA-3', that lie between these two regions may play an important role in substrate recognition, metal coordination, or other aspects of catalytic function.

It is further anticipated that an all-RNA molecule, other RNA-DNA composites, and molecules containing one or more nucleotide analogs may be acceptable substrates. As disclosed herein, the within-described in vitro evolution procedures may successfully be used to generate enzymatic DNA molecules having the desired specificities; further analyses along these lines are presently underway.

In addition, studies to determine whether the presumed base-pairing interactions between enzyme and substrate are generalizable with respect to sequence are in progress, using the presently-described methods. The within-disclosed $Pb^{2+}$-dependent deoxyribozymes may also be considered model compounds for exploring the structural and enzymatic properties of DNA.

The methods employed in the present disclosure for the rapid development of DNA catalysts will have considerable generality, allowing us to utilize other cofactors to trigger the cleavage of a target linkage attached to a potential catalytic domain. In this regard, the development of $Mg^{2+}$-dependent DNA enzymes that specifically cleave target RNAs under physiological conditions is of interest. Such a molecule will provide an alternative to traditional antisense and ribozyme approaches for the specific inactivation of target mRNAs.

DNA thus joins RNA and protein on the list of biological macromolecules that are capable of exhibiting enzymatic activity. The full extent of DNA's catalytic abilities remains to be explored, but these explorations should proceed rapidly based on in vitro selection methods such as those employed in this study.

DNA enzymes offer several important advantages compared to other macromolecular catalysts. First, they are easy to prepare, in an era when most laboratories have access to an automated DNA synthesizer and the cost of DNA phosphoramidites has become quite modest. Second, they are very stable compounds, especially compared to RNA, thus facilitating their use in biophysical studies. Third, we expect that they can be adapted to therapeutic applications that at present make use of antisense DNAs that lack RNA-cleavage activity. In vitro selection could be carried out with DNA analogues, including compounds that are nuclease resistant such as phosphorothioate-containing DNA, so long as these analogues can be prepared in the form of a deoxynucleoside 5'-triphosphate and are accepted as a substrate by a DNA-dependent DNA polymerase. Finally, DNA enzymes offer a new window on our understanding of the macromolecular basis of catalytic function. It will be interesting, for example, to carry out comparative analyses of protein-, RNA-, and DNA-based enzymes that catalyze the same chemical transformation.

Example 4

Other Families of Catalytic DNAs

Figure 5:
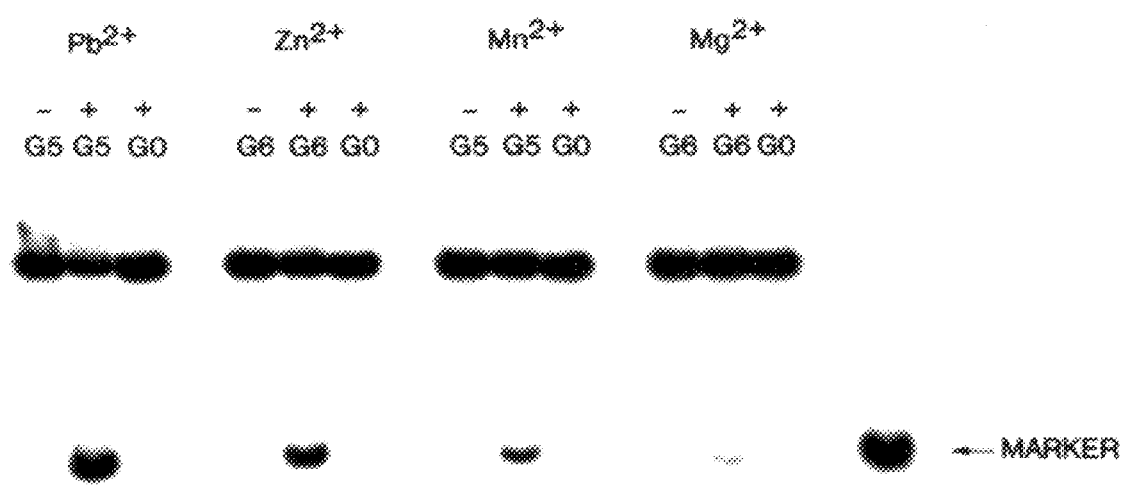
FIG. 5 is a photographic representation showing a polyacrylamide gel demonstrating specific endoribonuclease activity of four families of selected catalytic DNAs. Selection of a $Pb^{2+}$-dependent family of molecules was repeated in a side-by-side fashion as a control (first group). In the second group, $Zn^{2+}$ is used as the cation; in group three, the cation is $Mn^{2+}$; and in the fourth group, the cation is $Mg^{2+}$. A fifth site on the gel consists of the cleavage product alone, as a marker.

A starting pool of DNA was prepared by PCR essentially as described in Example 2.B. above, except that the starting pool of DNA comprised molecules containing 40 random nucleotides. Thus, the starting pool of DNA described herein was prepared by PCR using the synthetic oligomer 5' GGG ACG AAT TCT AAT ACG ACT CAC TAT rA GG AAG AGA TGG CGA CAT CTC $N_{40}$GT GAC GGT AAG CTT GGC AC 3' (SEQ ID NO 23), where N is an equimolar mixture of G, A, T and C, and where the DNA molecules were selected for the ability to cleave the phosphoester following the target rA. (See FIG. 6A, also.) Selective amplification was carried out in the presence of either $Pb^{2+}$, $Zn^{2+}$, $Mn^{2+}$, or $Mg^{2+}$, thereby generating at least four "families" of catalytic DNA molecules. As illustrated in FIG. 5, catalytic DNA molecules demonstrating specific activity were generated in the presence of a variety of cations.

FIG. 5 is a photographic representation showing a polyacrylamide gel demonstrating specific endoribonuclease activity of four families of selected catalytic DNAs. Selection of a $Pb^{2+}$-dependent family of molecules was repeated in a side-by-side fashion as a control. In each group of three lanes, the first lane shows the lack of activity of the selected population in the absence of the metal cation, the second lane shows the observed activity in the presence of the metal cation, and the third lane shows the lack of activity of the starting pool (G0). At present, the order of reactivity is observed to be $Pb^{2+}>Zn^{2+}>Mn^{2+}>Mg^{2+}$, mirroring the $pK_a$ of the corresponding metal-hydroxide.

After either five (G5) or six (G6) rounds of selective amplification in the presence of the preselected divalent cation, the desired endonuclease activity was obtained. The following description of selective amplification in the presence of $Mg^{2+}$ is intended to be exemplary.

Six rounds of in vitro selective amplification were carried out, following the method described in Example 2 hereinabove, except that the divalent metal used was 1 mM $Mg^{2+}$ rather than 1 mM $Pb^{2+}$. (See also Breaker and Joyce, *Chem. & Biol.* 1: 223–229 (1994), incorporated by reference herein, which describes essentially the same procedure.)

Individual clones were isolated following the sixth round, and the nucleotide sequence of 24 of these clones was determined. All of the sequences began with: 5' GGG ACG AAT TCT AAT ACG ACT CAC TAT rA GG AAG AGA TGG CGA CA (SEQ ID NO 23 from position 1 to 44) and ended with: CGG TAA GCT TGG CAC 3' (SEQ ID NO 23 from position 93 to 107).

The segment in the middle, corresponding to TCTC $N_{40}$ GTGA (SEQ ID NO 23 from position 45 to 92) in the starting pool, varied as follows:

(13) CCG CCC ACC TCT TTT ACG AGC CTG TAC GAA ATA GTG CTC TTG TTA GTA T (SEQ ID NO 24)

(5) TCT CTT CAG CGA TGC ACG CTT GTT TTA ATG TTG CAC CCA TGT TAG TGA (SEQ ID NO 25)

(2) TCT CAT CAG CGA TTG AAC CAC TTG GTG GAC AGA CCC ATG TTA GTG A (SEQ ID NO 26)

(1) CCG CCC ACC TCT TTT ACG AGC CTG TAC GAA ATA GTG TTC TTG TTA GTA T (SEQ ID NO 27)

(1) CCG CCC ACC TCT TTT ACG AGC CTG TAC GAA ATA GTG CTC TCG TTA GTA T (SEQ ID NO 28)

(1) TCT CAG ACT TAG TCC ATC ACA CTC TGT GCA TAT GCC TGC TTG ATG TGA (SEQ ID NO 29)

(1) -CT CTC ATC TGC TAG CAC GCT CGA ATA GTG TCA GTC GAT GTG A (SEQ ID NO 30).

The initial number in parentheses indicates the number of clones having that particular sequence. Note that some mutations (highlighted in bold type) occurred at nucleotide positions other than those that were randomized initially.

The second sequence listed above (i.e., SEQ ID NO 25), which occurred in 5 of 24 clones, was chosen as a lead compound for further study. Its cleavage activity was measured in the presence of a 1 mM concentration of various divalent metals and 1M NaCl at pH 7.0 and 23° C.:

| metal | $k_{obs}$ (min$^{-1}$) |
|---|---|
| none | n.d. |
| $Mg^{2+}$ | $2.3 \times 10^{-3}$ |
| $Mn^{2+}$ | $6.8 \times 10^{-3}$ |
| $Zn^{2+}$ | $4.2 \times 10^{-2}$ |
| $Pb^{2+}$ | $1.1 \times 10^{-2}$ |

Thus, the lead compound is active in the presence of all four divalent metals, even though it was selected for activity in the presence of $Mg^{2+}$. Conversely, DNA molecules that were selected for activity in the presence of $Mn^{2+}$, $Zn^{2+}$, or $Pb^{2+}$ did not show any activity in the presence of $Mg^{2+}$.

In addition, the population of DNAs obtained after six rounds of in vitro selection in the presence of $Mg^{2+}$, when prepared as all-phosphorothioate- containing DNA analogues, showed $Mg^{2+}$-dependent cleavage activity at an observed rate of ~$10^{-3}$ min$^{-1}$. The phosphorothioate-containing analogues were prepared enzymatically so as to have an $R_p$ configuration at each stereocenter. Such compounds are relatively resistant to degradation by cellular nucleases compared to unmodified DNA.

The lead compound was re-randomized at 40 nucleotide positions (underlined), introducing mutations at a frequency of 15% (5% probability of each of the three possible base substitutions). The re-randomized population was subjected to seven additional rounds of in vitro selection. During the last four rounds, molecules that were reactive in the presence of 1 mM $Pb^{2+}$ were removed from the population before the remainder were challenged to react in the presence of 1 mM $Mg^{2+}$. Individual clones were isolated following the seventh round and the nucleotide sequence of 14 of these clones was determined. All of the , sequences began with: 5' GGG ACG AAT TCT AAT ACG ACT CAC TAT rA GG AAG AGA TGG CGA CAT CTC (SEQ ID NO 23, from position 1 to 48), and ended with: GTG ACG GTA AGC TTG GCA C 3' (SEQ ID NO 23, from position 89 to 107).

The segment in the middle, corresponding to the 40 partially-randomized positions ($N_{40}$, SEQ ID NO 23, from position 49 to 88), varied as follows:

(4) TAC AGC GAT TCA CCC TTG TTT AAG GGT TAC ACC CAT GTT A (SEQ ID NO 31)

(2) ATC AGC GAT TAA CGC TTG TTT CAA TGT TAC ACC CAT GTT A (SEQ ID NO 32)

(2) TTC AGC GAT TAA CGC TTA TTT TAG CGT TAC ACC CAT GTT A (SEQ ID NO 33)

(1) ATC AGC GAT TCA CCC TTG TTT TAA GGT TGC ACC CAT GTT A (SEQ ID NO 34)

(1) ATC AGC GAT TCA CCC TTG TTT AAG CGT TAC ACC CAT GTT G (SEQ ID NO 35)

(1) ATC AGC GAT TCA CCC TTG TTT TAA GGT TAC ACC CAT GTT A (SEQ ID NO 36)

(1) ATC AGC GAT TAA CGC TTA TTT TAG CGT TAC ACC CAT GTT A (SEQ ID NO 37)

(1) ATC AGC GAT TAA CGC TTG TTT TAG TGT TGC ACC CAT GTT A (SEQ ID NO 38)

(1) ATC AGC GAT TAA CGC TTA TTT TAG CAT TAC ACC CAT GTT A (SEQ ID NO 39).

The number in parentheses indicates the number of clones having that particular sequence. Nucleotides shown in bold are those that differ compared to the lead compound.

Formal analysis of the cleavage activity of these clones is ongoing. The population as a whole exhibits $Mg^{2+}$-dependent cleavage activity at an observed rate of ~$10^{-2}$ min$^{-1}$, with a comparable level of activity in the presence of $Pb^{2+}$.

FIGS. 6A and 6B provide two-dimensional illustrations of a "progenitor" catalytic DNA molecule and one of several catalytic DNA molecules obtained via the selective amplification methods disclosed herein, respectively. FIG. 6A illustrates an exemplary molecule from the starting pool, showing the overall configuration of the molecules represented by SEQ ID NO 23. As illustrated, various complementary nucleotides flank the random ($N_{40}$) region.

FIG. 6B is a diagrammatic representation of one of the $Mg^{2+}$-dependent catalytic DNA molecules (or "DNAzymes") generated via the within-described procedures (SEQ ID NO 40). The location of the ribonucleotide in the substrate nucleic acid is indicated via the arrow. (The illustrated molecule includes the sequence identified herein as SEQ ID NO 25, as well as "beginning" and "ending" sequences of SEQ ID NO 23.)

Endonuclease activity is continuing to be enhanced in each of the aforementioned "families" via in vitro evolution, as disclosed herein, so it is anticipated that enzymatic DNA molecules of increasingly desirable specificities may be generated successfully using the within-disclosed guidelines.

The foregoing specification, including the specific embodiments and examples, is intended to be illustrative of the present invention and is not to be taken as limiting. Numerous other variations and modifications can be effected without departing from the true spirit and scope of the present invention.

We claim:

1. A catalytic DNA molecule having site-specific endonuclease activity, wherein said catalytic DNA molecule comprises a nucleotide sequence selected from the group consisting of:
SEQ ID NO 3;
SEQ ID NO 14;
SEQ ID NO 15;
SEQ ID NO 16;
SEQ ID NO 17;
SEQ ID NO 18;
SEQ ID NO 19;
SEQ ID NO 20;
SEQ ID NO 21; and
SEQ ID NO 22.

2. The catalytic DNA molecule of claim 1, wherein said endonuclease activity is enhanced by the presence of $Mg^{2+}$.

3. The catalytic DNA molecule of claim 1, wherein said endonuclease activity is enhanced by the presence of a cation selected from the group consisting of $Pb^{2+}$, $Mn^{2+}$, $Zn^{2+}$, $Ca^{2+}$, $Na^+$, and $K^+$.

4. A catalytic DNA molecule having site-specific endonuclease activity, wherein said catalytic DNA molecule comprises a nucleotide sequence selected from the group consisting of:
SEQ ID NO 23;
SEQ ID NO 24;
SEQ ID NO 25;
SEQ ID NO 26;
SEQ ID NO 27;
SEQ ID NO 28;
SEQ ID NO 29;
SEQ ID NO 30;
SEQ ID NO 31;
SEQ ID NO 32;
SEQ ID NO 33;
SEQ ID NO 34;
SEQ ID NO 35;
SEQ ID NO 36;
SEQ ID NO 37;
SEQ ID NO 38; and
SEQ ID NO 39.

5. The catalytic DNA molecule of claim 4, wherein said endonuclease activity is enhanced by the presence of $Mg^{2+}$.

6. The catalytic DNA molecule of claim 4, wherein said endonuclease activity is enhanced by the presence of a cation selected from the group consisting of $Pb^{2+}$, $Mn^{2+}$, $Zn^{2+}$, $Ca^{2+}$, $Na^+$, and $K^+$.

7. A catalytic DNA molecule that specifically cleaves a substrate nucleic acid at a defined cleavage site, said catalytic DNA molecule produced by a method comprising the steps of:
    a. admixing a population of single-stranded DNA molecules with ribonucleotide-containing substrate nucleic acid molecules to form an admixture;
    b. maintaining said admixture for a sufficient period of time and under predetermined reaction conditions to allow single-stranded DNA molecules in said population to cause cleavage of said substrate nucleic acid molecules, thereby producing substrate cleavage products; and
    c. isolating single-stranded PND molecules that cleave said substrate nucleic acid molecules from said population.

8. The catalytic DNA molecule of claim 7, wherein said defined cleavage site comprises a single-stranded nucleic acid.

9. The catalytic DNA molecule of claim 7, wherein said substrate comprises RNA, DNA, modified RNA, modified DNA, nucleotide analogs, or composites thereof.

10. The catalytic DNA molecule of claim 7, wherein said catalytic DNA molecule catalyzes hydrolytic cleavage of a phosphoester bond at said cleavage site.

11. The catalytic DNA molecule of claim 7, wherein said catalytic DNA molecule is single-stranded.

12. The catalytic DNA molecule of claim 7, wherein said substrate nucleic acid is attached to said catalytic DNA molecule.

13. The catalytic DNA molecule of claim 7, wherein said catalytic DNA molecule has a substrate binding affinity of about 1 $\mu$M or less.

14. The catalytic DNA molecule of claim 7, wherein said catalytic DNA molecule binds substrate with a $K_D$ of less than about 0.1 μM.

15. The catalytic DNA molecule of claim 7, wherein said catalytic DNA molecule includes a conserved nucleotide core comprising one or more conserved nucleotide sequences.

16. A composition comprising two or more populations of catalytic DNA molecules according to claim 7, wherein each population of catalytic DNA molecules cleaves a substrate nucleic acid at a different cleavage site.

17. A composition comprising a catalytic DNA molecule according to claim 7 and a cation.

18. A method of cleaving a phosphoester bond in a substrate, comprising:
   a. admixing the catalytic DNA molecule of claim 7 with phosphoester bond-containing substrate, to form a reaction admixture;
   b. maintaining said admixture under predetermined reaction conditions to allow said catalytic DNA molecule to cleave said phosphoester bonds, thereby producing a population of cleavage products; and
   c. separating said cleavage products from said catalytic DNA molecule.

19. A method of specifically cleaving a nucleic acid-containing substrate at a specific cleavage site, comprising the steps of:
   a. contacting the catalytic DNA molecule of claim 7 with said substrate to form an admixture; and
   b. maintaining said admixture for a time period sufficient to permit cleavage of said substrate.

20. The catalytic DNA molecule of claim 10, wherein said hydrolytic cleavage is further enhanced by the presence of a monovalent or divalent cation.

21. The catalytic DNA molecule of claim 15, wherein said one or more conserved nucleotide sequences are selected from the group consisting of:
   CG;
   CGA;
   AGCG;
   AGCCG;
   CAGCGAT;
   CTTGTTT; and
   CTTATTT.

22. The catalytic DNA molecule of claim 15, wherein said conserved core includes at least two conserved nucleotide sequences, and wherein said catalytic DNA molecule further comprises one or more variable or spacer nucleotides interspersed between said conserved nucleotide sequences in said conserved core.

23. The catalytic DNA molecule of claim 15, further comprising one or more substrate binding nucleotide sequences.

24. The composition according to claim 16, further comprising a cation.

25. The composition according to claim 17, wherein said cation is selected from the group consisting of $Pb^{2+}$, $MG^{2+}$, $Mn^{2+}$, $Zn^{2+}$, $Ca^{2+}$, $Na^+$, and $K^+$.

26. The method of claim 18, wherein said predetermined reaction conditions include the addition of monovalent or divalent cations.

27. The method of claim 19, further comprising the addition of a cation to said admixture.

28. The catalytic DNA molecule of claim 20, wherein said cation is selected from the group consisting of $Pb^{2+}$, $Mg^{2+}$, $Mn^{2+}$, $Zn^{2+}$, $Ca^{2+}$, $Na^+$, and $K^+$.

29. The catalytic DNA molecule of claim 23, wherein said one or more substrate binding nucleotide sequences flank said conserved nucleotide core.

30. The catalytic DNA molecule of claim 23, wherein said one or more substrate binding nucleotide sequences are selected from the group consisting of:
   CATCTCT;
   GCTCT;
   TTGCTTTTT;
   TGTCTTCTC;
   TTGCTGCT;
   GCCATGCTTT (SEQ ID NO 19, residues 5–14);
   CTCTATTTCT (SEQ ID NO 20, residues 10–19):
   GTCGGCA;
   CATCTCTTC; and
   ACTTCT.

31. The catalytic DNA molecule of claim 23, wherein said one or more substrate binding nucleotide sequences are selected from the group consisting of:
   TATGTGACGCTA (SEQ ID NO 14, residues 28–39);
   TATAGTCGTA (SEQ ID NO 15, residues 41–50);
   ATAGCGTATTA (SEQ ID NO 16, residues 40–50);
   ATAGTTACGTCAT (SEQ ID NO 17, residues 27–39);
   AATAGTGAAGTGTT (SEQ ID NO 18, residues 28–41);
   TATAGTGTA;
   ATAGTCGGT;
   ATAGGCCCGGT (SEQ ID NO 21, residues 40–50);
   AATAGTGAGGCTTG (SEQ ID NO 22, residues 36–49); and
   ATGNTG.

32. The catalytic DNA molecule of claim 23, wherein said one or more substrate binding nucleotide sequences are selected from the group consisting of:
   TGTT;
   TGTTA; and
   TGTTAG.

33. The catalytic DNA molecule of claim 23, further comprising one or more variable or spacer nucleotides that:
   a. are intercalated between said conserved core and an adjacent substrate binding nucleotide sequence; or
   b. are intercalated between conserved nucleotide sequences in said conserved core; or
   c. are intercalated between adjacent substrate binding nucleotide sequences; or
   d. are located at either or both termini of said catalytic DNA molecule; or
   e. any combination of a, b, c, and d.

34. The composition according to claim 24, wherein said cation is selected from the group consisting of $pb^{2+}$, $Mg^{2+}$, $Zn^{2+}$, $Ca^{2+}$, $Na^+$, and $K^+$.

35. The method of claim 26, wherein said cations are selected from the group consisting of $Pb^{2+}$, $Mg^{2+}$, $Mn^{2+}$, $Zn^{2+}$, $Ca^{2+}$, $Na^{2+}$, and $K^+$.

36. A method of selecting a catalytic DNA molecule that cleaves a substrate nucleic acid at a specific site, comprising the steps of:
   a. admixing a population of single-stranded DNA molecules with ribonucleotide-containing substrate nucleic acid molecules, to form an admixture;
   b. maintaining said admixture for a sufficient period of time and under predetermined reaction conditions to allow single-stranded DNA molecules in said population to cause cleavage of said substrate nucleic acid molecules, thereby producing substrate cleavage products; and c. isolating single-stranded DNA molecules that cleave said substrate nucleic acid molecules from said population.

37. The method of claim 36, wherein said DNA molecules are tagged with an immobilizing agent.

38. The method of claim 37, wherein said agent comprises biotin.

39. The method of claim 38, wherein said isolating step further comprises exposing said tagged DNA molecules to a solid surface having avidin linked thereto, whereby said tagged DNA molecules become attached to said solid surface.

40. An enzymatic DNA molecule comprising a deoxyribonucleotide polymer having a catalytic activity for cleaving a nucleic acid-containing substrate to produce a cleavage product said enzymatic DNA molecule produced by a method comprising the steps of:

a. admixing a population of single-stranded DNA molecules with ribonucleotide-containing substrate nucleic acid molecules to form an admixture;

b. maintaining said admixture for a sufficient period of time and under predetermined reaction conditions to allow single-stranded DNA molecules in said population to cause cleavage of said substrate nucleic acid molecules, thereby producing substrate cleavage products; and c. isolating single-stranded DNA molecules that cleave said substrate nucleic acid molecules from said population.

41. The enzymatic DNA molecule according to claim 40, wherein said enzymatic DNA molecule has a binding affinity for said substrate and lacks a binding affinity for said cleavage product.

42. An enzymatic DNA molecule comprising a conserved domain flanked by two substrate binding domains, said enzymatic DNA molecule produced by a method comprising the steps of:

a. admixing a population of single-stranded DNA molecules with ribonucleotide-containing substrate nucleic acid molecules, to form an admixture;

b. maintaining said admixture for a sufficient period of time and under predetermined reaction conditions to allow single-stranded DNA molecules in said population to-cause cleavage of said substrate nucleic acid molecules, thereby producing substrate cleavage products; and c. isolating single-stranded DNA molecules that cleave said substrate nucleic acid molecules from said population.

* * * * *

SEQUENCE LISTING ( 1 ) GENERAL INFORMATION:

( i i i ) NUMBER OF SEQUENCES: 40

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

CGGTAAGCTT GGCAC       15

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_difference
        ( B ) LOCATION: replace(8, "")
        ( D ) OTHER INFORMATION: /standard_name= "ADENOSINE
            RIBONUCLEOTIDE"

( x i ) SEQUENCE DESCRIPTION: SEQ ID NO:2:

TCACTATNAG GAAGAGATGG       20

( 2 ) INFORMATION FOR SEQ ID NO:3:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

ACACATCTCT GAAGTAGCGC CGCCGTATAG TGACGCTA       38

( 2 ) INFORMATION FOR SEQ ID NO:4:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GTGCCAAGCT TACCGNNNNN NNNNNNNNNN NNNNNNNNNN NNNNNNNNNN NNNNNNNNNN       60

NNNNGTCGC CATCTCTTCC       80

( 2 ) INFORMATION FOR SEQ ID NO:5:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature (B) LOCATION: 28
                (D) OTHER INFORMATION: /standard_name= "2'3'CYCLIC
                    PHOSPHATE"

(ix) FEATURE:
                (A) NAME/KEY: misc_difference
                (B) LOCATION: replace(28, "")
                (D) OTHER INFORMATION: /standard_name= "ADENOSINE
                    RIBONUCLEOTIDE"

(xi) SEQUENCE DESCRIPTION: SEQ ID NO:5:

GGGACGAATT CTAATACGAC TCACTATN                                          28

(2) INFORMATION FOR SEQ ID NO:6:

(i) SEQUENCE CHARACTERISTICS:
                (A) LENGTH: 28 base pairs
                (B) TYPE: nucleic acid
                (C) STRANDEDNESS: single
                (D) TOPOLOGY: linear (ii) MOLECULE TYPE: DNA (genomic)

(ix) FEATURE:
                (A) NAME/KEY: misc_difference
                (B) LOCATION: replace(28, "")
                (D) OTHER INFORMATION: /standard_name= "ADENOSINE
                    RIBONUCLEOTIDE"

(xi) SEQUENCE DESCRIPTION: SEQ ID NO:6:

GGGACGAATT CTAATACGAC TCACTATN                                          28

(2) INFORMATION FOR SEQ ID NO:7:

(i) SEQUENCE CHARACTERISTICS:
                (A) LENGTH: 19 base pairs
                (B) TYPE: nucleic acid
                (C) STRANDEDNESS: single
                (D) TOPOLOGY: linear (ii) MOLECULE TYPE: DNA (genomic)

(ix) FEATURE:
                (A) NAME/KEY: misc_difference
                (B) LOCATION: replace(8, "")
                (D) OTHER INFORMATION: /standard_name= "ADENOSINE
                    RIBONUCLEOTIDE"

(xi) SEQUENCE DESCRIPTION: SEQ ID NO:7:

TCACTATNGG AAGAGATGG                                                    19

(2) INFORMATION FOR SEQ ID NO:8:

(i) SEQUENCE CHARACTERISTICS:
                (A) LENGTH: 8 base pairs
                (B) TYPE: nucleic acid
                (C) STRANDEDNESS: single
                (D) TOPOLOGY: linear (ii) MOLECULE TYPE: DNA (genomic)

(ix) FEATURE:
                (A) NAME/KEY: misc_difference
                (B) LOCATION: replace(8, "")
                (D) OTHER INFORMATION: /standard_name= "ADENOSINE
                    NUCLEOTIDE"

(xi) SEQUENCE DESCRIPTION: SEQ ID NO:8:

TCACTATN                                                                 8

(2) INFORMATION FOR SEQ ID NO:9:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:9:

CCATCTCTTC CTATAGTGAG TCCGGCTGCA 30

( 2 ) INFORMATION FOR SEQ ID NO:10:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

GTGCCAAGCT TACCG 15

( 2 ) INFORMATION FOR SEQ ID NO:11:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

CTGCAGAATT CTAATACGAC TCACTATAGG AAGAGATGGC GAC 43

( 2 ) INFORMATION FOR SEQ ID NO:12:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_difference
        ( B ) LOCATION: replace(8, "")
        ( D ) OTHER INFORMATION: /standard_name= "ADENOSINE RIBONUCLEOTIDE"

( x i ) SEQUENCE DESCRIPTION: SEQ ID NO:12:

TCACTATNGG AAGAGATGG 19

( 2 ) INFORMATION FOR SEQ ID NO:13:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_difference
        ( B ) LOCATION: replace(28, "")
        ( D ) OTHER INFORMATION: /standard_name= "ADENOSINE RIBONUCLEOTIDE"

( x i ) SEQUENCE DESCRIPTION: SEQ ID NO:13:

GGGACGAATT CTAATACGAC TCACTATNGG AAGAGATGGC GAC    43

( 2 ) INFORMATION FOR SEQ ID NO:14:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

TCACACATCT CTGAAGTAGC GCCGCCGTAT GTGACGCTAG GGGTTCGCCT    50

( 2 ) INFORMATION FOR SEQ ID NO:15:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

GGGGGGAACG CCGTAACAAG CTCTGAACTA GCGGTTGCGA TATAGTCGTA    50

( 2 ) INFORMATION FOR SEQ ID NO:16:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

CGGGACTCCG TAGCCCATTG CTTTTTGCAG CGTCAACGAA TAGCGTATTA    50

( 2 ) INFORMATION FOR SEQ ID NO:17:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

CCACCATGTC TTCTCGAGCC GAACCGATAG TTACGTCATA CCTCCCGTAT    50

( 2 ) INFORMATION FOR SEQ ID NO:18:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

GCCAGATTGC TGCTACCAGC GGTACGAAAT AGTGAAGTGT TCGTGACTAT    50

( 2 ) INFORMATION FOR SEQ ID NO:19:

( i ) SEQUENCE CHARACTERISTICS:
　　　　　　　　( A ) LENGTH: 50 base pairs
　　　　　　　　( B ) TYPE: nucleic acid
　　　　　　　　( C ) STRANDEDNESS: single
　　　　　　　　( D ) TOPOLOGY: linear ( i i ) MOLECULE TYPE: DNA (genomic)

( x i ) SEQUENCE DESCRIPTION: SEQ ID NO:19:

ATAGGCCATG CTTTGGCTAG CGGCACCGTA TAGTGTACCT GCCCTTATCG　　　　　　　　50

( 2 ) INFORMATION FOR SEQ ID NO:20:

( i ) SEQUENCE CHARACTERISTICS:
　　　　　　　　( A ) LENGTH: 50 base pairs
　　　　　　　　( B ) TYPE: nucleic acid
　　　　　　　　( C ) STRANDEDNESS: single
　　　　　　　　( D ) TOPOLOGY: linear ( i i ) MOLECULE TYPE: DNA (genomic)

( x i ) SEQUENCE DESCRIPTION: SEQ ID NO:20:

TCTGCTCTCC TCTATTCTAG CAGTGCAGCG AAATATGTCG AATAGTCGGT　　　　　　　　50

( 2 ) INFORMATION FOR SEQ ID NO:21:

( i ) SEQUENCE CHARACTERISTICS:
　　　　　　　　( A ) LENGTH: 50 base pairs
　　　　　　　　( B ) TYPE: nucleic acid
　　　　　　　　( C ) STRANDEDNESS: single
　　　　　　　　( D ) TOPOLOGY: linear ( i i ) MOLECULE TYPE: DNA (genomic)

( x i ) SEQUENCE DESCRIPTION: SEQ ID NO:21:

TTGCCCAGCA TAGTCGGCAG ACGTGGTGTT AGCGACACGA TAGGCCCGGT　　　　　　　　50

( 2 ) INFORMATION FOR SEQ ID NO:22:

( i ) SEQUENCE CHARACTERISTICS:
　　　　　　　　( A ) LENGTH: 50 base pairs
　　　　　　　　( B ) TYPE: nucleic acid
　　　　　　　　( C ) STRANDEDNESS: single
　　　　　　　　( D ) TOPOLOGY: linear ( i i ) MOLECULE TYPE: DNA (genomic)

( x i ) SEQUENCE DESCRIPTION: SEQ ID NO:22:

TTGCTAGCTC GGCTGAACTT CTGTAGCGCA ACCGAAATAG TGAGGCTTGA　　　　　　　　50

( 2 ) INFORMATION FOR SEQ ID NO:23:

( i ) SEQUENCE CHARACTERISTICS:
　　　　　　　　( A ) LENGTH: 107 base pairs
　　　　　　　　( B ) TYPE: nucleic acid
　　　　　　　　( C ) STRANDEDNESS: single
　　　　　　　　( D ) TOPOLOGY: linear ( i i ) MOLECULE TYPE: DNA (genomic)

( i x ) FEATURE:
　　　　　　　　( A ) NAME/KEY: misc_difference
　　　　　　　　( B ) LOCATION: replace(28, "")
　　　　　　　　( D ) OTHER INFORMATION: /standard_name= "ADENOSINE
　　　　　　　　　　　　RIBONUCLEOTIDE"
　　　　　　　　　　／ label= rA ( x i ) SEQUENCE DESCRIPTION: SEQ ID NO:23:

GGGACGAATT CTAATACGAC TCACTATNGG AAGAGATGGC GACATCTCNN NNNNNNNNNN　　　　60

NNNNNNNNN NNNNNNNNN NNNNNNNGT GACGGTAAGC TTGGCAC     107

( 2 ) INFORMATION FOR SEQ ID NO:24:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

CCGCCCACCT CTTTTACGAG CCTGTACGAA ATAGTGCTCT TGTTAGTAT     49

( 2 ) INFORMATION FOR SEQ ID NO:25:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

TCTCTTCAGC GATGCACGCT TGTTTTAATG TTGCACCCAT GTTAGTGA     48

( 2 ) INFORMATION FOR SEQ ID NO:26:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

TCTCATCAGC GATTGAACCA CTTGGTGGAC AGACCCATGT TAGTGA     46

( 2 ) INFORMATION FOR SEQ ID NO:27:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

CCGCCCACCT CTTTTACGAG CCTGTACGAA ATAGTGTTCT TGTTAGTAT     49

( 2 ) INFORMATION FOR SEQ ID NO:28:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

CCGCCCACCT CTTTTACGAG CCTGTACGAA ATAGTGCTCT CGTTAGTAT     49

( 2 ) INFORMATION FOR SEQ ID NO:29:

( i ) SEQUENCE CHARACTERISTICS:
    ( A ) LENGTH: 48 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:29:

TCTCAGACTT AGTCCATCAC ACTCTGTGCA TATGCCTGCT TGATGTGA     48

( 2 ) INFORMATION FOR SEQ ID NO:30:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

CTCTCATCTG CTAGCACGCT CGAATAGTGT CAGTCGATGT GA     42

( 2 ) INFORMATION FOR SEQ ID NO:31:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

TACAGCGATT CACCCTTGTT TAAGGGTTAC ACCCATGTTA     40

( 2 ) INFORMATION FOR SEQ ID NO:32:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

ATCAGCGATT AACGCTTGTT TCAATGTTAC ACCCATGTTA     40

( 2 ) INFORMATION FOR SEQ ID NO:33:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:33:

TTCAGCGATT AACGCTTATT TTAGCGTTAC ACCCATGTTA     40

( 2 ) INFORMATION FOR SEQ ID NO:34:

( i ) SEQUENCE CHARACTERISTICS:
        ( A ) LENGTH: 40 base pairs
        ( B ) TYPE: nucleic acid
        ( C ) STRANDEDNESS: single ( D ) TOPOLOGY: linear ( i i ) MOLECULE TYPE: DNA (genomic)

( x i ) SEQUENCE DESCRIPTION: SEQ ID NO:34:

ATCAGCGATT CACCCTTGTT TTAAGGTTGC ACCCATGTTA 40

( 2 ) INFORMATION FOR SEQ ID NO:35:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:35:

ATCAGCGATT CACCCTTGTT TAAGCGTTAC ACCCATGTTG 40

( 2 ) INFORMATION FOR SEQ ID NO:36:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:36:

ATCAGCGATT CACCCTTGTT TTAAGGTTAC ACCCATGTTA 40

( 2 ) INFORMATION FOR SEQ ID NO:37:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:37:

ATCAGCGATT AACGCTTATT TTAGCGTTAC ACCCATGTTA 40

( 2 ) INFORMATION FOR SEQ ID NO:38:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:38:

ATCAGCGATT AACGCTTGTT TTAGTGTTGC ACCCATGTTA 40

( 2 ) INFORMATION FOR SEQ ID NO:39:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:39:

```
ATCAGCGATT  AACGCTTATT  TTAGCATTAC  ACCCATGTTA                                        4 0
```

( 2 ) INFORMATION FOR SEQ ID NO:40:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_difference
        ( B ) LOCATION: replace(19, "")
        ( D ) OTHER INFORMATION: /standard_name= "ADENOSINE
                RIBONUCLEOTIDE"

( x i ) SEQUENCE DESCRIPTION: SEQ ID NO:40:

```
CTAATACGAC  TCACTATANG  GAAGAGATGG  CGACATCTCT  TCAGCGATGC  ACGCTTGTTT                 6 0

TAATGTTGCA  CCCATGTTAG                                                                8 0
```